(12) United States Patent
Lee et al.

(10) Patent No.: US 10,032,990 B2
(45) Date of Patent: Jul. 24, 2018

(54) ORGANIC COMPOSITION, AND ORGANIC OPTOELECTRONIC ELEMENT AND DISPLAY DEVICE

(71) Applicant: SAMSUNG SDI CO., LTD., Yongin-si, Gyeonggi-do (KR)

(72) Inventors: Han-Ill Lee, Suwon-si (KR); Ji-Hun Shin, Suwon-si (KR); Dong-Kyu Ryu, Suwon-si (KR); Eun-Sun Yu, Suwon-si (KR); Su-Jin Han, Suwon-si (KR); Jin-Seok Hong, Suwon-si (KR)

(73) Assignee: SAMSUNG SDI CO., LTD., Yongin-si, Gyeonggi-do (KR)

(*) Notice: Subject to any disclaimer, the term of this patent is extended or adjusted under 35 U.S.C. 154(b) by 313 days.

(21) Appl. No.: 14/786,379

(22) PCT Filed: Feb. 20, 2014

(86) PCT No.: PCT/KR2014/001391
§ 371 (c)(1),
(2) Date: Oct. 22, 2015

(87) PCT Pub. No.: WO2015/005559
PCT Pub. Date: Jan. 15, 2015

(65) Prior Publication Data
US 2016/0072073 A1    Mar. 10, 2016

(30) Foreign Application Priority Data

Jul. 10, 2013 (KR) .................. 10-2013-0081176

(51) Int. Cl.
*H01L 51/50* (2006.01)
*H01L 51/00* (2006.01)
(Continued)

(52) U.S. Cl.
CPC ........ *H01L 51/0067* (2013.01); *C07D 213/06* (2013.01); *C07D 213/16* (2013.01);
(Continued)

(58) Field of Classification Search
None
See application file for complete search history.

(56) References Cited

U.S. PATENT DOCUMENTS

| | | |
|---|---|---|
| 2006/0115680 A1 | 6/2006 | Hwang et al. |
| 2011/0073845 A1 | 3/2011 | Tseng et al. |

(Continued)

FOREIGN PATENT DOCUMENTS

| | | |
|---|---|---|
| EP | 1 661 888 A1 | 5/2006 |
| JP | 2002-043061 A | 2/2002 |

(Continued)

OTHER PUBLICATIONS

Zhou, et al., "Selective Oxidative Cyclization by $FeCl_3$ in the Construction of 10H-Indeno[1,2-b]triphenylene Skeletons in Polycyclic Aromatic Hydrocarbons", Journal of Organic Chemistry 2006, 71(18), pp. 6822-6828.

(Continued)

*Primary Examiner* — Gregory D Clark
(74) *Attorney, Agent, or Firm* — Lee & Morse, P.C.

(57) ABSTRACT

Disclosed are an organic compound represented by a combination of a moiety represented by Chemical Formula 1 and a moiety represented by Chemical Formula 2, an organic optoelectronic device and a display device including the organic compound.

11 Claims, 1 Drawing Sheet

(51) Int. Cl.
| | |
|---|---|
| *C07D 405/04* | (2006.01) |
| *C07D 251/24* | (2006.01) |
| *C09K 11/06* | (2006.01) |
| *C07D 405/14* | (2006.01) |
| *C07D 239/26* | (2006.01) |
| *C07D 405/10* | (2006.01) |
| *C07D 409/04* | (2006.01) |
| *C07D 409/10* | (2006.01) |
| *C07D 409/14* | (2006.01) |
| *C07D 213/06* | (2006.01) |
| *C07D 213/16* | (2006.01) |
| *C09K 11/02* | (2006.01) |

(52) U.S. Cl.
CPC ......... *C07D 239/26* (2013.01); *C07D 251/24* (2013.01); *C07D 405/04* (2013.01); *C07D 405/10* (2013.01); *C07D 405/14* (2013.01); *C07D 409/04* (2013.01); *C07D 409/10* (2013.01); *C07D 409/14* (2013.01); *C09K 11/025* (2013.01); *C09K 11/06* (2013.01); *H01L 51/0054* (2013.01); *H01L 51/0056* (2013.01); *H01L 51/0073* (2013.01); *H01L 51/0074* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *H01L 51/006* (2013.01); *H01L 51/0072* (2013.01); *H01L 51/0081* (2013.01); *H01L 51/0085* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 2251/552* (2013.01)

(56) References Cited

U.S. PATENT DOCUMENTS

| | | |
|---|---|---|
| 2011/0266526 A1 | 11/2011 | Ma et al. |
| 2012/0075171 A1 | 3/2012 | Hashimoto et al. |
| 2013/0048975 A1 | 2/2013 | Hong et al. |
| 2013/0099206 A1 | 4/2013 | Jung et al. |
| 2015/0001489 A1* | 1/2015 | Lee ................... H01L 51/0054 257/40 |

FOREIGN PATENT DOCUMENTS

| | | |
|---|---|---|
| JP | 2009-114068 A | 5/2009 |
| JP | 2012-059904 A | 3/2012 |
| JP | 2012-131752 A | 7/2012 |
| JP | 2013-010703 A | 1/2013 |
| KR | 10-2010-0063713 A | 6/2010 |
| KR | 10-2011-0041729 A | 4/2011 |
| KR | 10-1134575 B1 | 4/2012 |
| KR | 10-2012-0072784 A | 7/2012 |
| KR | 10-1196093 B1 | 11/2012 |
| KR | 10-2013-0006029 A | 1/2013 |
| KR | 10-2013-0007934 A | 1/2013 |
| KR | 10-2013-0007951 A | 1/2013 |
| KR | 10-1218029 B1 | 1/2013 |
| KR | 10-2014-0135524 A | 11/2014 |
| KR | 10-2015-0003599 A | 1/2015 |
| WO | WO 2012/086366 A1 | 6/2012 |
| WO | WO 2013/001997 A1 | 1/2013 |
| WO | WO 2013/009079 A1 | 1/2013 |

OTHER PUBLICATIONS

Extended European Search Report dated Jan. 26, 2017, of the corresponding European Patent Application No. 14823854.6.
Chinese Search Report dated Aug. 18, 2016 for CN 201480039630.8; Lee, et al.

* cited by examiner

[Figure 1]
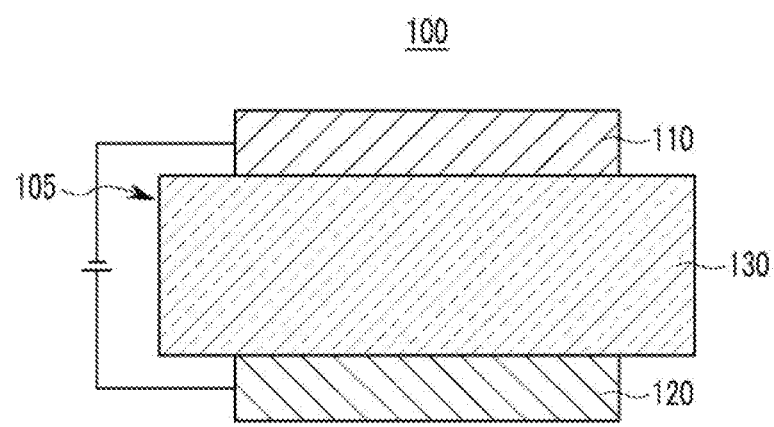
[Figure 2]
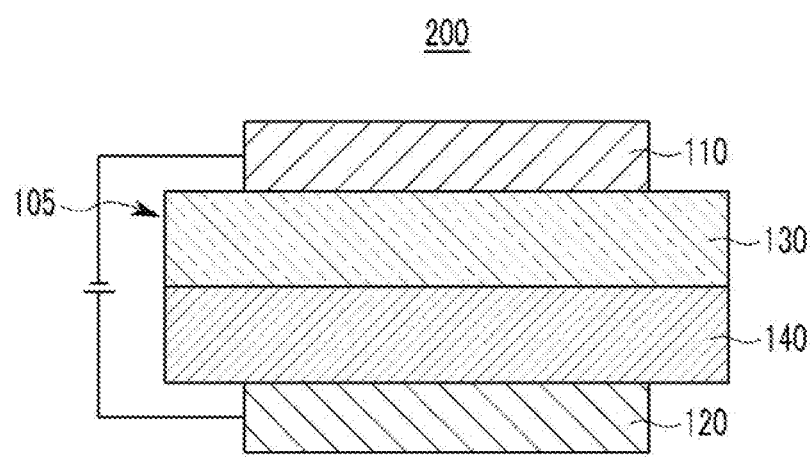

ORGANIC COMPOSITION, AND ORGANIC OPTOELECTRONIC ELEMENT AND DISPLAY DEVICE

CROSS REFERENCE TO RELATED APPLICATIONS

This is the U.S. national phase application based on PCT Application No. PCT/KR2014/001391, filed Feb. 20, 2014, which is based on Korean Patent Application No. 10-2013-0081176, filed Jul. 10, 2013, the entire contents of all of which are hereby incorporated by reference.

TECHNICAL FIELD

An organic compound, an organic optoelectronic device and a display device are disclosed.

BACKGROUND ART

An organic optoelectronic device is a device that converts electrical energy into photoenergy, and vice versa.

An organic optoelectronic device may be classified as follows in accordance with its driving principles. One is an optoelectronic device where excitons are generated by photoenergy, separated into electrons and holes the electrons and holes, and are transferred to different electrodes to generate electrical energy, and the other is a light emitting device where a voltage or a current is supplied to an electrode to generate photoenergy from electrical energy.

Examples of an organic optoelectronic device may be an organic photoelectric device, an organic light emitting diode, an organic solar cell and an organic photo conductor drum.

Of these, an organic light emitting diode (OLED) has recently drawn attention due to an increase in demand for flat panel displays. Such an organic light emitting diode converts electrical energy into light by applying current to an organic light emitting material. It has a structure in which an organic layer is interposed between an anode and a cathode. Herein, an organic layer may include an emission layer and optionally an auxiliary layer, and the auxiliary layer may include, for example at least one selected from a hole injection layer, a hole transport layer, an electron blocking layer, an electron transport layer, an electron injection layer, and a hole blocking layer in order increase efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

One embodiment provides an organic compound being capable of realizing an organic optoelectronic device having high efficiency and long life-span.

Another embodiment provides an organic optoelectronic device including the organic compound.

Yet another embodiment provides a display device including the organic optoelectronic device.

Technical Solution

According to one embodiment, an organic compound represented by a combination of a moiety represented by Chemical Formula 1 and a moiety represented by Chemical Formula 2 is provided:

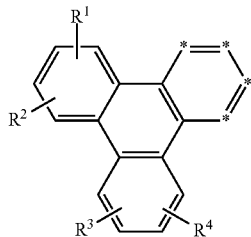

[Chemical Formula 1]

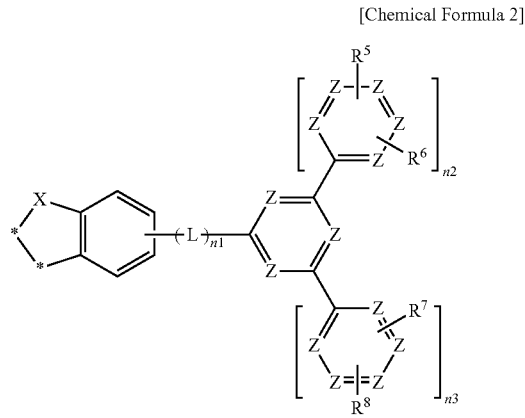

[Chemical Formula 2]

In Chemical Formula 1 or Chemical Formula 2,

X is $CR^aR^b$, $SiR^cR^d$, O, S, SO, or $SO_2$,

Z is each independently N or $CR^e$, at least one of Z is N, $R^1$ to $R^8$ and $R^a$ to $R^e$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, L is a substituted or unsubstituted C1 to C20 alkylene group, a substituted or unsubstituted C6 to C30 arylene group, a substituted or unsubstituted C3 to C30 heteroarylene group, or a combination thereof, n1 to n3 are each independently 0 or 1, and adjacent two *'s of Chemical Formula 1 are bonded with two *'s of Chemical Formula 2 to form a fused ring.

According to another embodiment, provided is an organic optoelectronic device that includes an anode and a cathode facing each other and at least one organic layer between the anode and the cathode, wherein the organic layer includes the organic compound.

Yet according to another embodiment, a display device including the organic optoelectronic device is provided.

Advantageous Effect

An organic optoelectronic device having high efficiency and long life-span may be realized.

DESCRIPTION OF DRAWINGS

FIGS. 1 and 2 are cross-sectional views showing organic light emitting diodes according to one embodiment.

BEST MODE

Hereinafter, embodiments of the present invention are described in detail. However, these embodiments are exemplary, and this disclosure is not limited thereto.

In the present specification, when a definition is not otherwise provided, the term "substituted" refers to one substituted with a substituent selected from deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C3 to C30 heterocycloalkyl group, a C6 to C30 aryl group, a C6 to C30 heteroaryl group, a C1 to C20 alkoxy group, a fluoro group, a C1 to C10 trifluoroalkyl group such as a trifluoromethyl group and the like, or a cyano group, instead of a substituent or a compound.

In addition, the adjacent two substituents selected from the substituted halogen, hydroxy group, an amino group, a substituted or unsubstituted C1 to C20 amine group, a nitro group, a substituted or unsubstituted C3 to C40 silyl group, C1 to C30 alkyl group, C1 to C10 alkylsilyl group, C3 to C30 cycloalkyl group, C3 to C30 heterocycloalkyl group, C6 to C30 aryl group, C6 to C30 heteroaryl group, C1 to C20 alkoxy group, fluoro group, C1 to C10 trifluoroalkyl group such as a trifluoromethyl group and the like, or cyano group may be fused to each other to form a ring. For example, the substituted C6 to C30 aryl group may be fused to another adjacent substituted C6 to C30 aryl group to form a substituted or unsubstituted fluorene ring.

In the present specification, when specific definition is not otherwise provided, "hetero" refers to one including 1 to 3 hetero atoms selected from N, O, S, P, and Si, and remaining carbons in one functional group.

In the present specification, when a definition is not otherwise provided, the term "combination thereof" refers to at least two substituents bound with each other by a linker, or at least two substituents condensed to each other.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, the term "aryl group" refers to a substituent including all element of the cycle having p-orbitals which form conjugation, and may be monocyclic, polycyclic or fused ring polycyclic (i.e., rings sharing adjacent pairs of carbon atoms) functional group.

In the present specification, the term "heteroaryl group" refers to aryl group including 1 to 3 heteroatoms selected from N, O, S, P and Si and remaining carbon. When the heteroaryl group is a fused ring, each ring may include 1 to 3 heteroatoms.

More specifically, a substituted or unsubstituted C6 to C30 aryl group and/or a substituted or unsubstituted C2 to C30 heteroaryl group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazole group, or a combination thereof, but is not limited thereto.

In the specification, hole characteristics refer to characteristics capable of donating an electron to form a hole when electric field is applied, and characteristics that holes formed in an anode are easily injected into an emission layer, and holes in the emission layer are easily transported to an anode and transported in the emission layer due to conductive characteristics according to HOMO level.

In addition, electron characteristics refer to characteristics capable of accepting an electron when electric field is applied, and characteristics that electrons formed in the cathode is easily injected into the emission layer, and electrons formed in the emission layer are easily transported to a cathode and transported in the emission layer due to conductive characteristics according to LUMO level.

Hereinafter, an organic compound according to one embodiment is described.

An organic compound according to one embodiment is represented by a combination of a moiety represented by Chemical Formula 1 and a moiety represented by Chemical Formula 2.

[Chemical Formula 1]

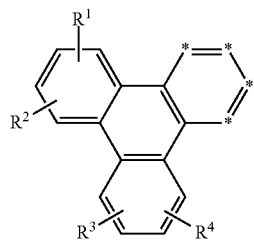

[Chemical Formula 3]

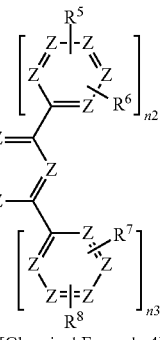

[Chemical Formula 2]

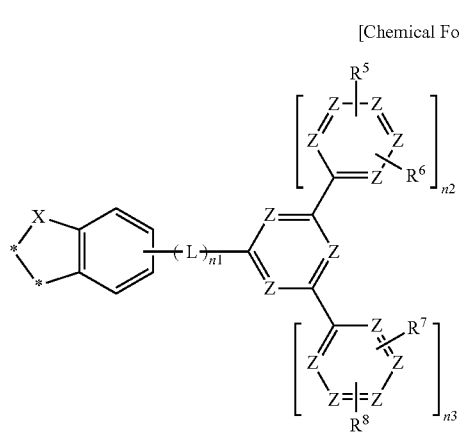

[Chemical Formula 4]

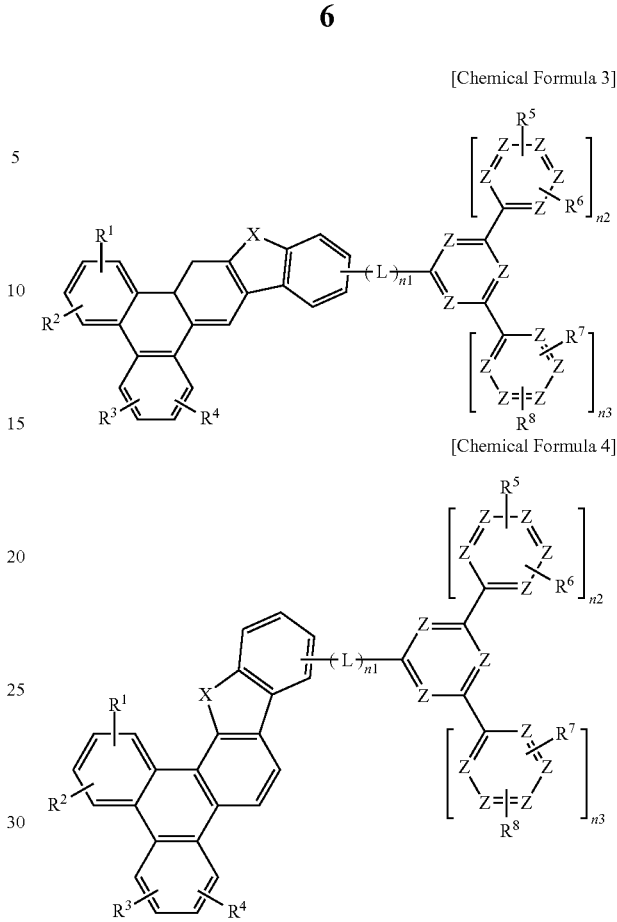

In Chemical Formula 1 or Chemical Formula 2,

X is $CR^aR^b$, $SiR^cR^d$, O, S, SO or $SO_2$,

Z is each independently N or $CR^e$, at least one of Z is N, $R^1$ to $R^8$ and $R^a$ to $R^e$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, L is a substituted or unsubstituted C1 to C20 alkylene group, a substituted or unsubstituted C6 to C30 arylene group, a substituted or unsubstituted C3 to C30 heteroarylene group, or a combination thereof, n1 to n3 are each independently 0 or 1, and adjacent two *'s of Chemical Formula 1 are bonded with two *'s of Chemical Formula 2 to form a fused ring.

The organic compound may be, for example represented by Chemical Formula 3 or Chemical Formula 4 depending on a bonding position of the moiety represented by Chemical Formula 1 and the moiety represented by Chemical Formula 2.

In Chemical Formula 3 or Chemical Formula 4,

X, Z, $R^1$ to $R^8$, and $R^a$ to $R^e$, L, and n1 to n3 are the same as described above.

The organic compound includes indenotriphenylene and at least one nitrogen-containing heteroaryl group.

The organic compound has a structure of easily accepting electrons when an electric field is applied due to at least one nitrogen-containing ring, and thus may decrease a driving voltage of an organic optoelectronic device including the organic compound.

The organic compound includes an indenotriphenylene moiety easily accepting holes and a nitrogen-containing ring moiety easily accepting electrons and thus, has a bipolar structure and balances between hole and electron flows and resultantly, may improve efficiency of an organic optoelectronic device including the organic compound.

The organic compound appropriately may localize the indenotriphenylene moiety easily accepting holes and the moiety easily accepting electrons and control a flow of a conjugated system and thus, show excellent bipolar characteristics. Accordingly, the organic compound may improve life-span of an organic optoelectronic device.

In addition, the organic compound has a structure of being able to effectively prevent stacking of the organic compounds and thus, may improve process stability and simultaneously, lower a deposition temperature.

The moiety represented by Chemical Formula 2 may be, for example represented by one of Chemical Formula 2-I to Chemical Formula 2-111:

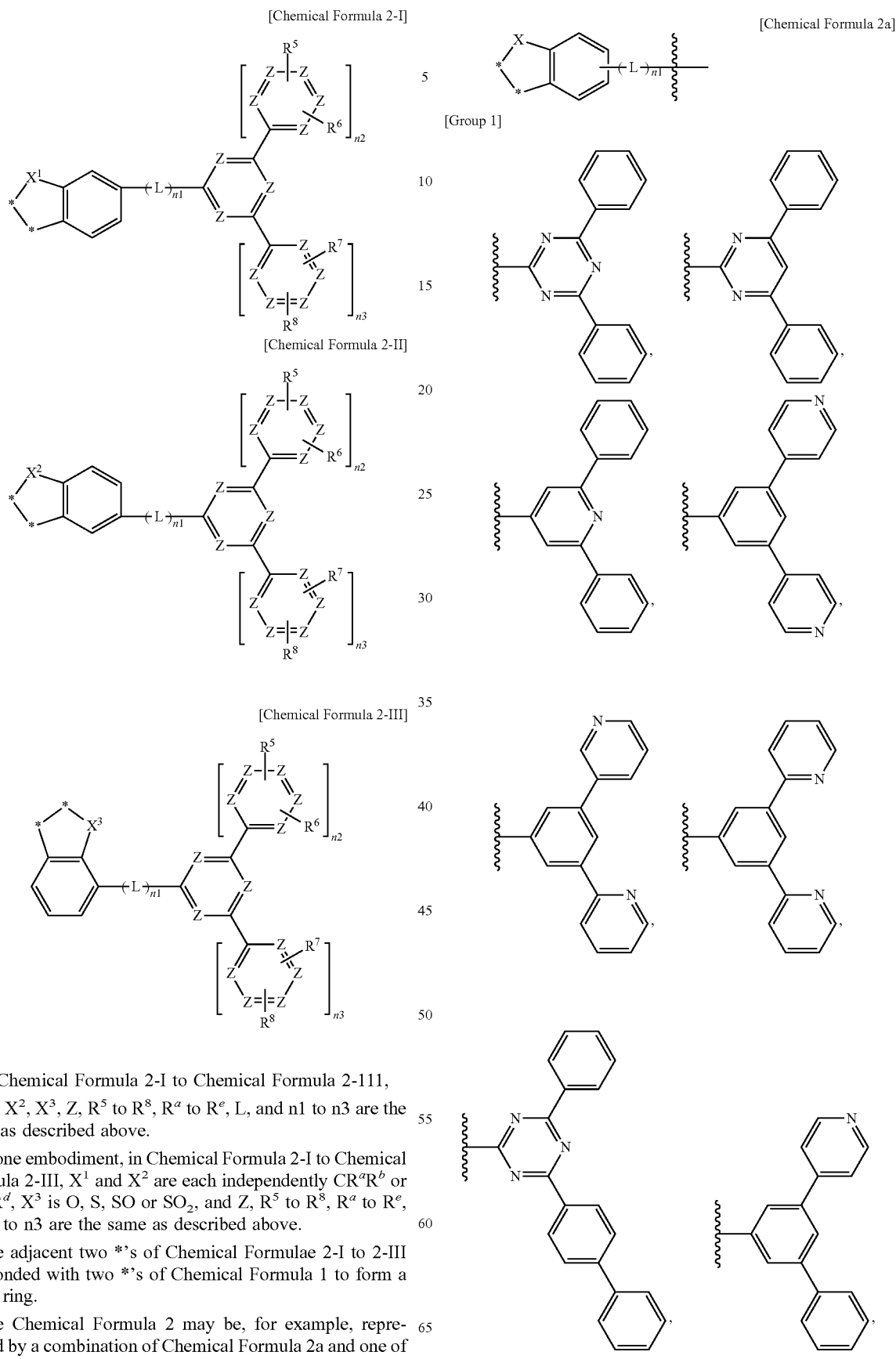

In Chemical Formula 2-I to Chemical Formula 2-111, $X^1$, $X^2$, $X^3$, Z, $R^5$ to $R^8$, $R^a$ to $R^e$, L, and n1 to n3 are the same as described above.

In one embodiment, in Chemical Formula 2-I to Chemical Formula 2-III, $X^1$ and $X^2$ are each independently $CR^aR^b$ or $SiR^cR^d$, $X^3$ is O, S, SO or $SO_2$, and Z, $R^5$ to $R^8$, $R^a$ to $R^e$, L, n1 to n3 are the same as described above.

The adjacent two *'s of Chemical Formulae 2-I to 2-III are bonded with two *'s of Chemical Formula 1 to form a fused ring.

The Chemical Formula 2 may be, for example, represented by a combination of Chemical Formula 2a and one of Group 1.

-continued

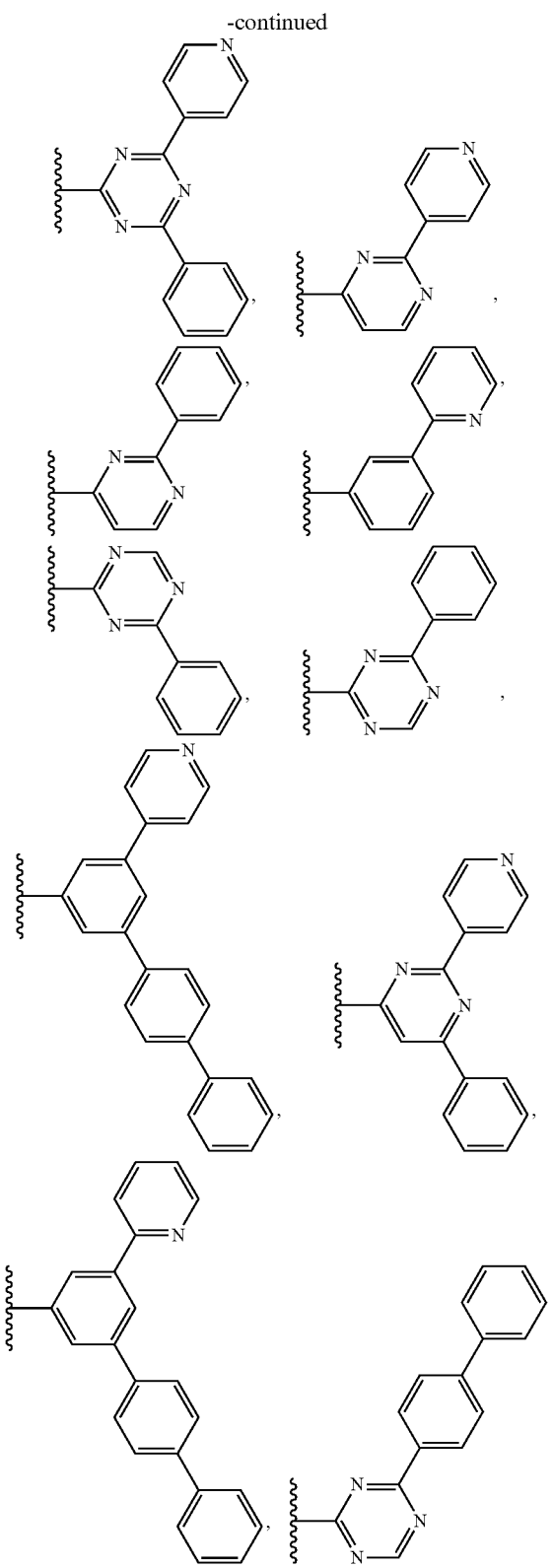

In Chemical Formula 2a or Group 1, X, $R^a$ to $R^d$, and L and n1 are the same as described above.

L of Chemical Formula 2 may be, for example a substituted or unsubstituted C6 to C30 arylene group, for example a substituted or unsubstituted phenylene group, a substituted or unsubstituted biphenylene group or a substituted or unsubstituted terphenylene group, but is not limited thereto.

For example, $R^1$ to $R^4$ of Chemical Formula 1 may each independently be hydrogen, deuterium or a substituted or unsubstituted C1 to C20 alkyl group.

The organic compound may be, for example a compound of Group 2, but is not limited thereto.

[Group 2]

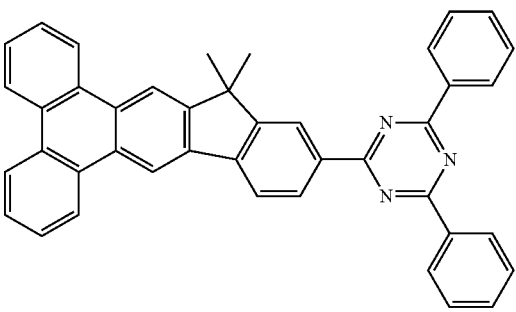

1

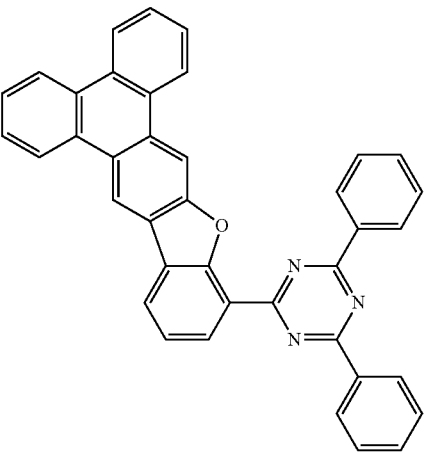

2

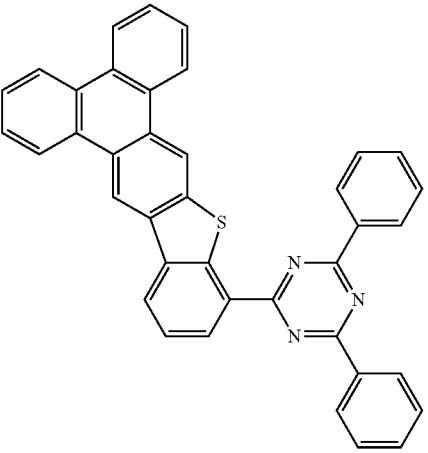

3

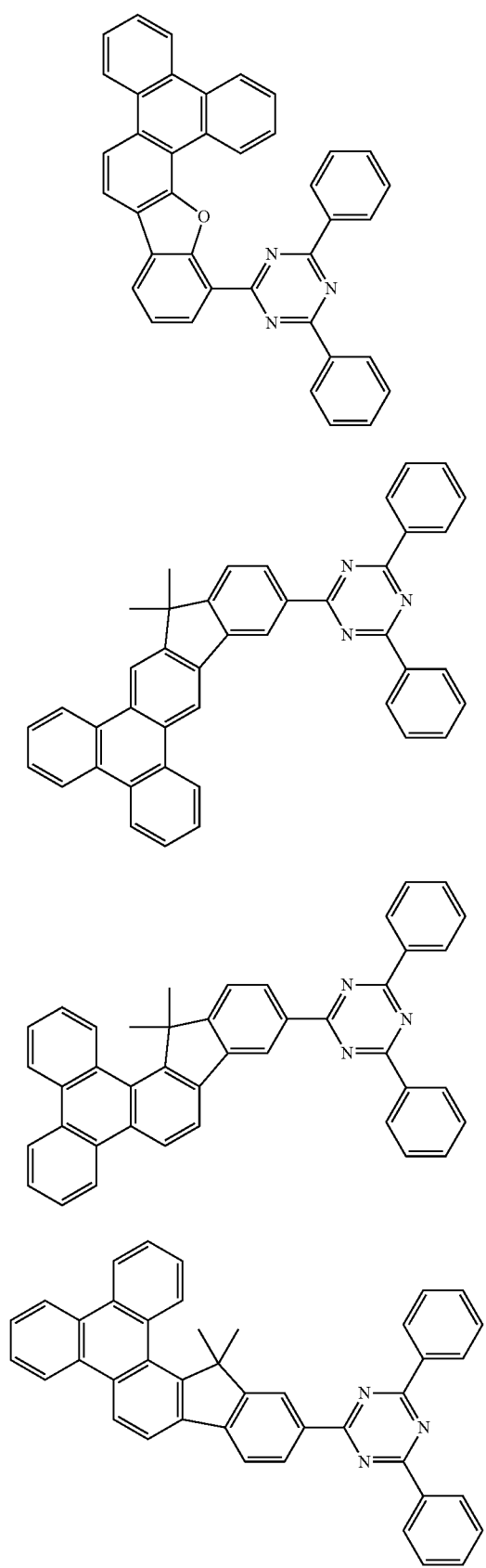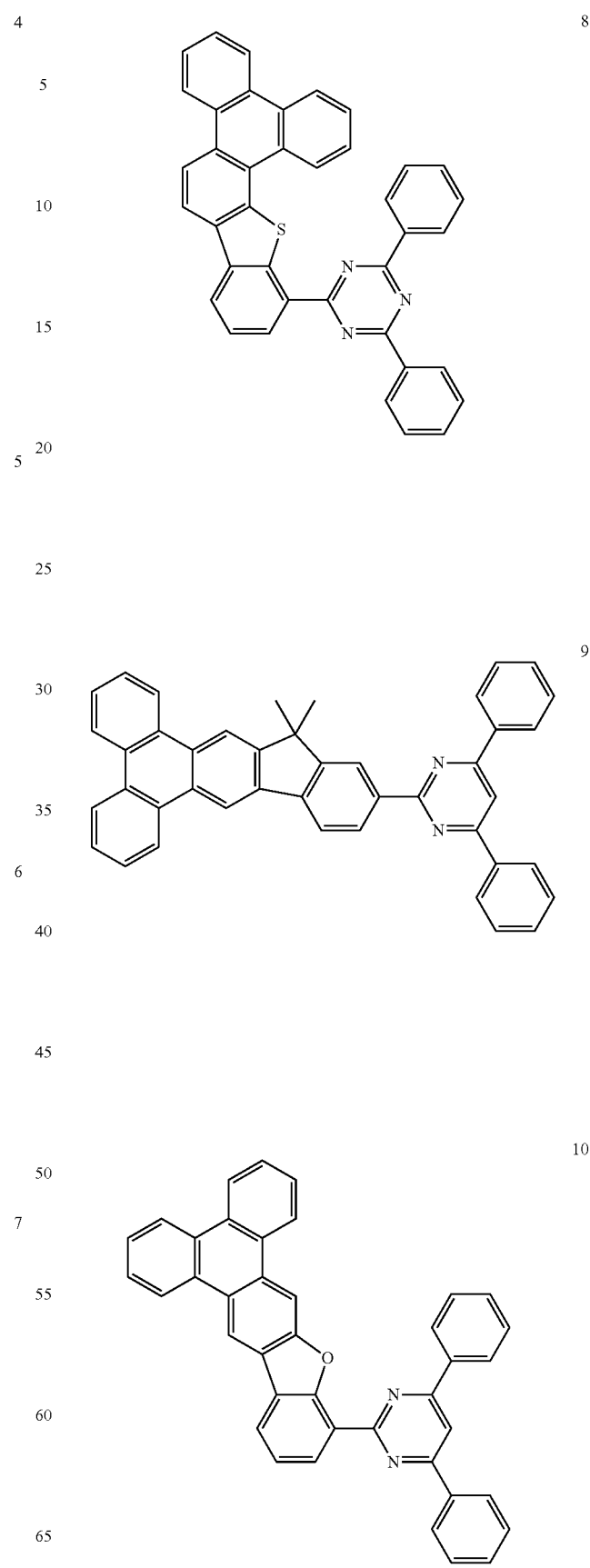

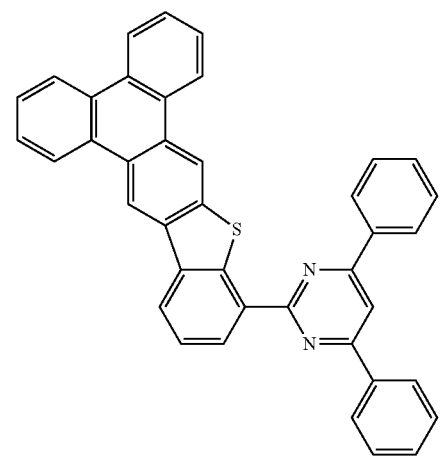
11
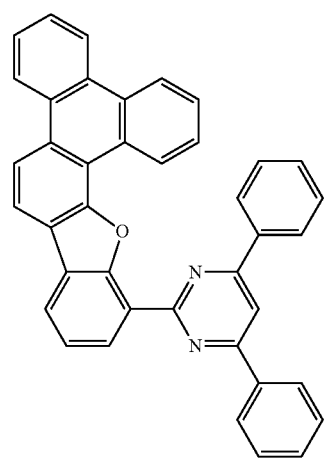
12
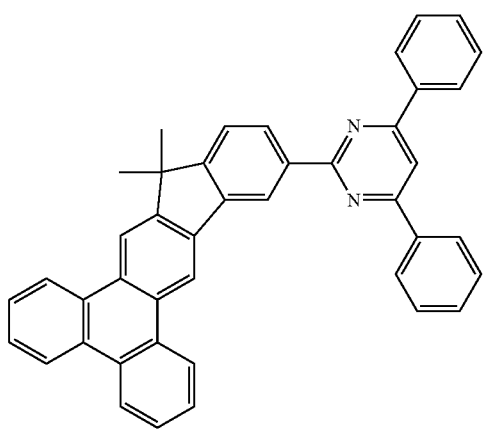
13
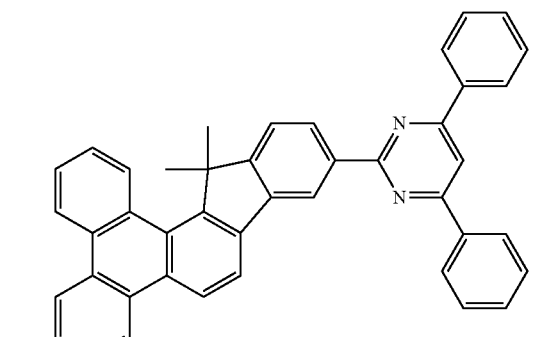
14
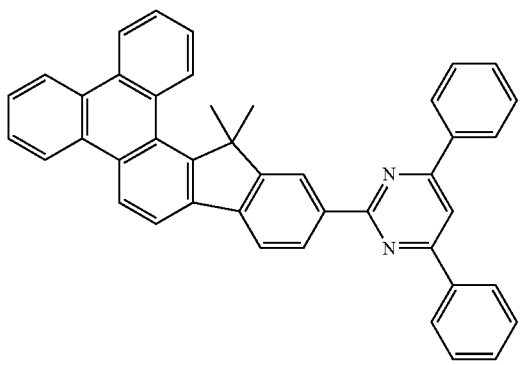
15
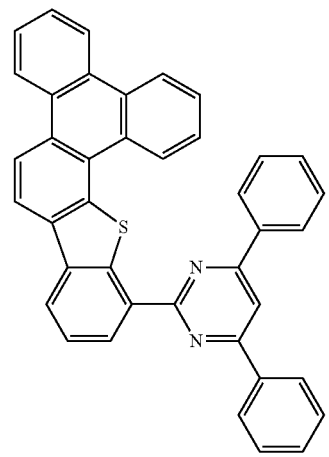
16
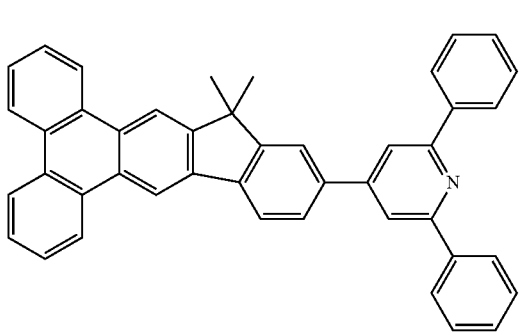
17

18
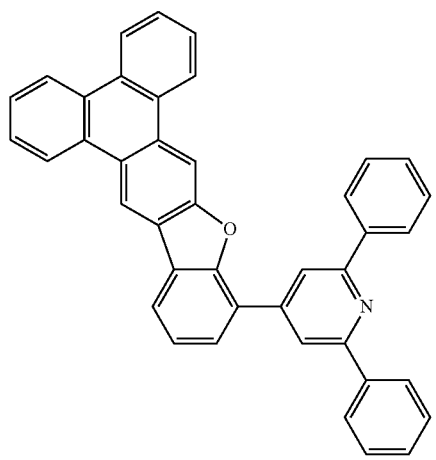
19
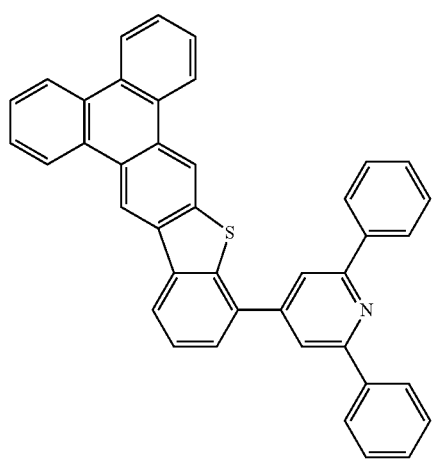
20
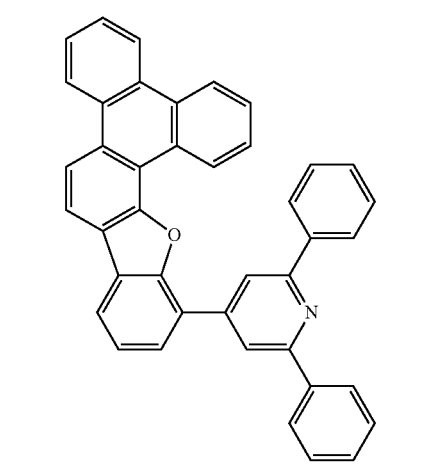
21
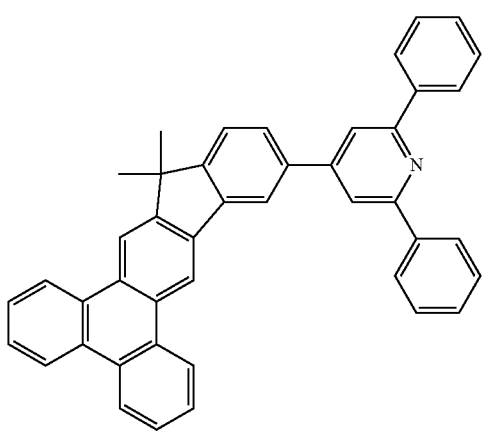
22
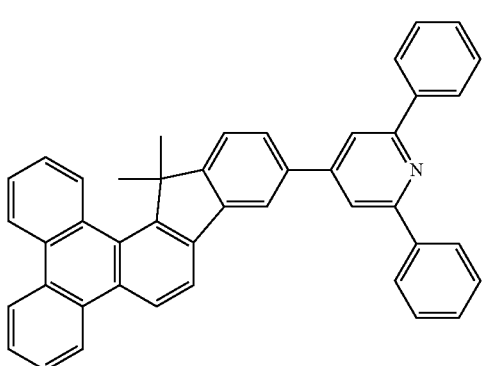
23
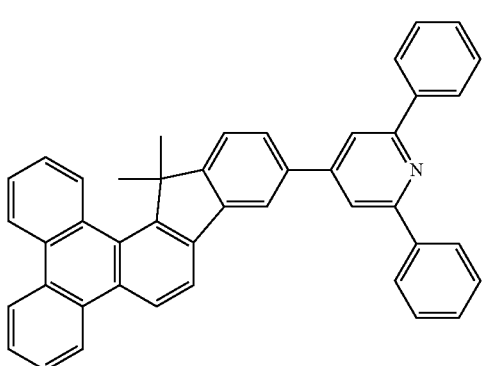
24
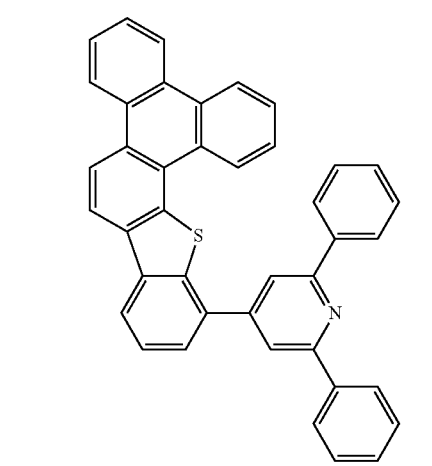

25
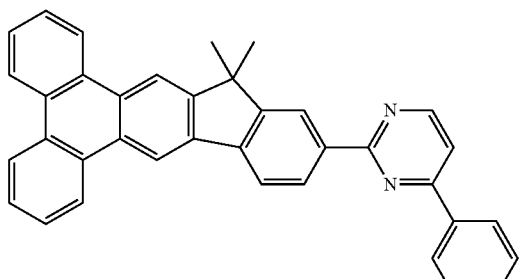
26
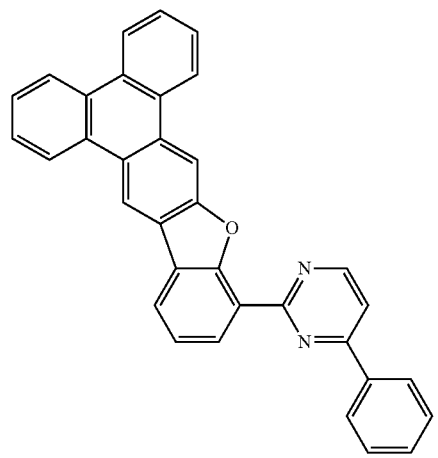
27
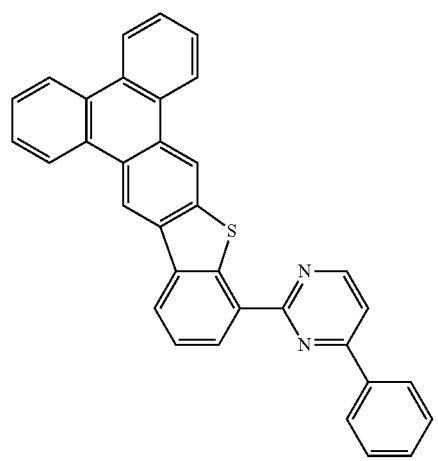
28
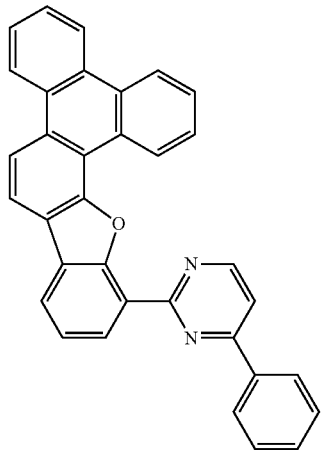
29
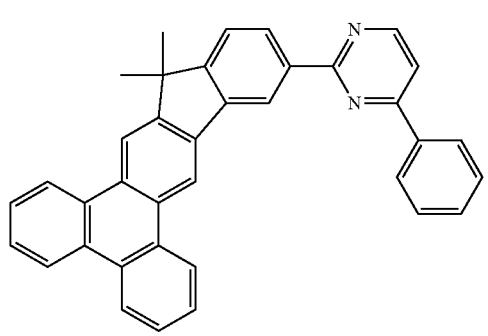
30
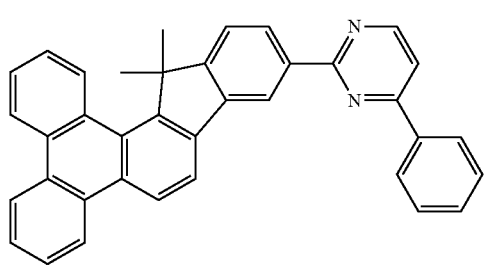
31

32
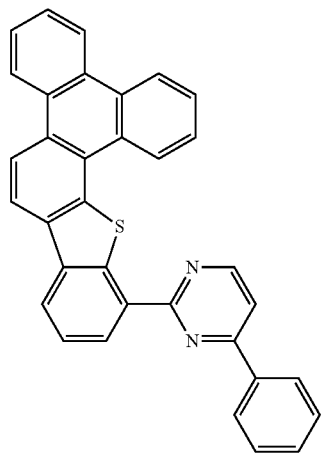
33
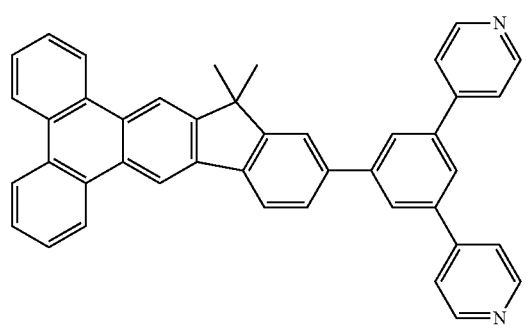
34
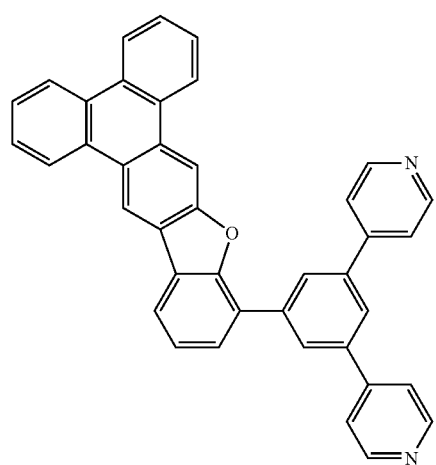
35
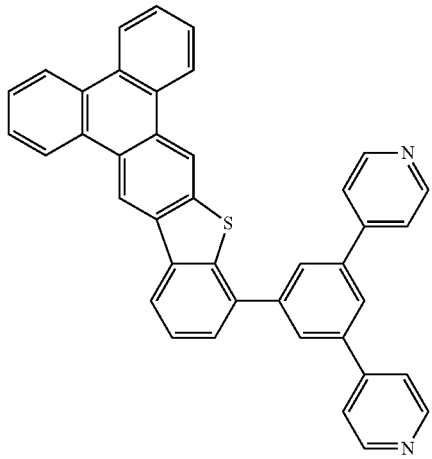
36
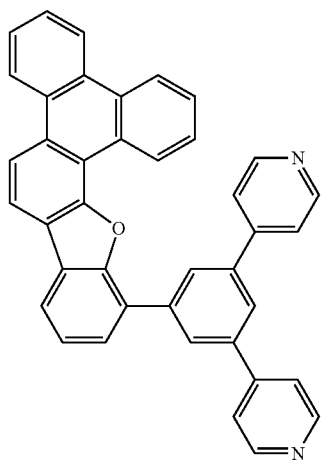
37
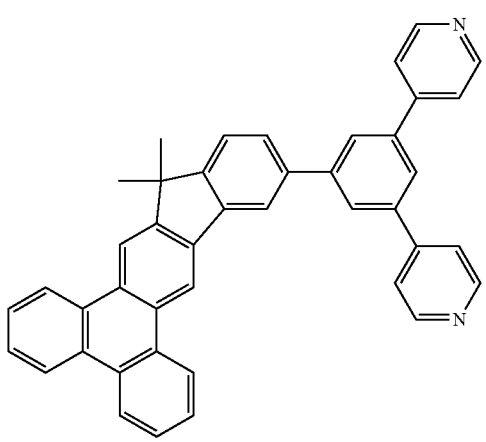

38
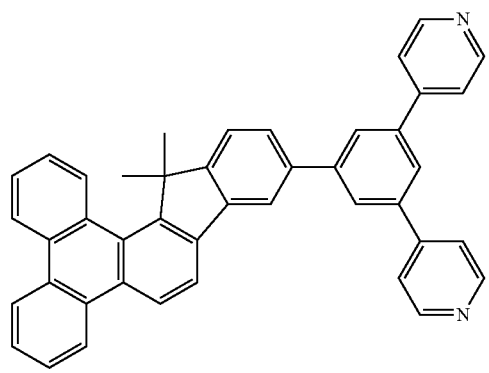
39
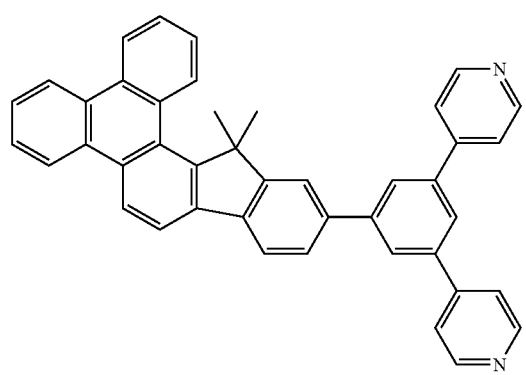
40
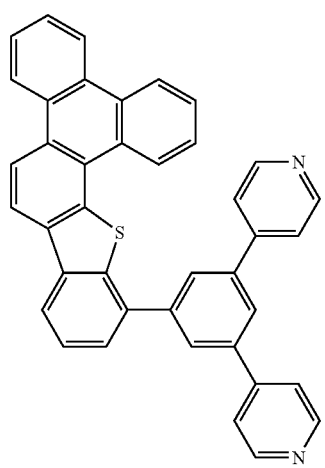
41
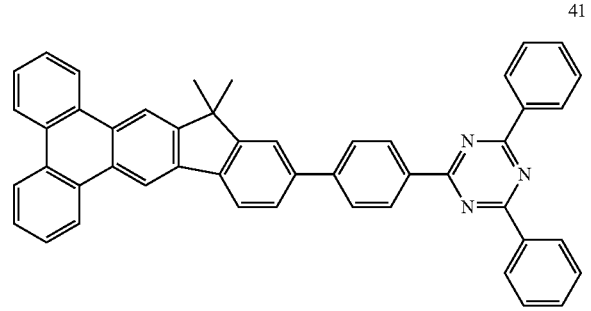
42
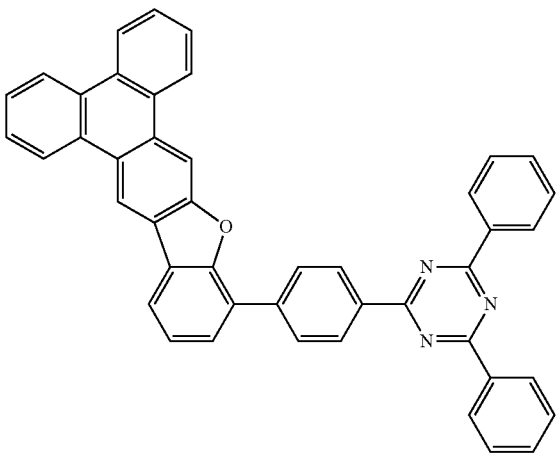
43
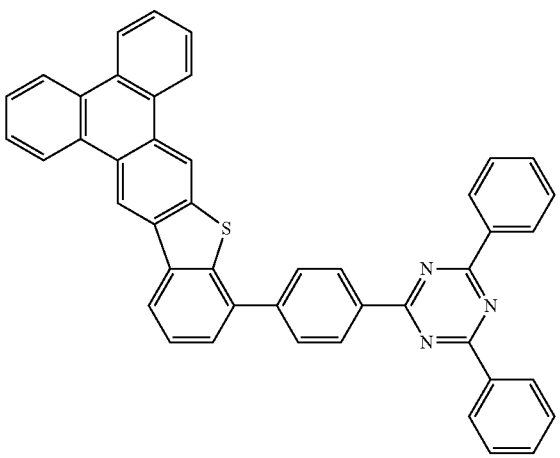
44
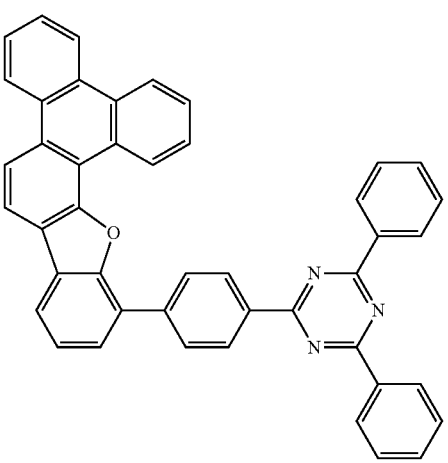

45
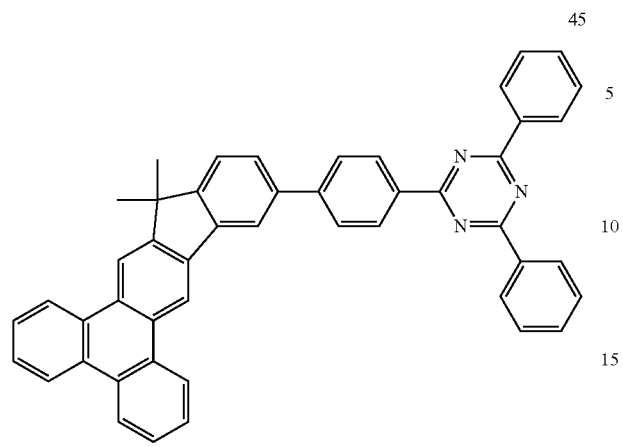
46
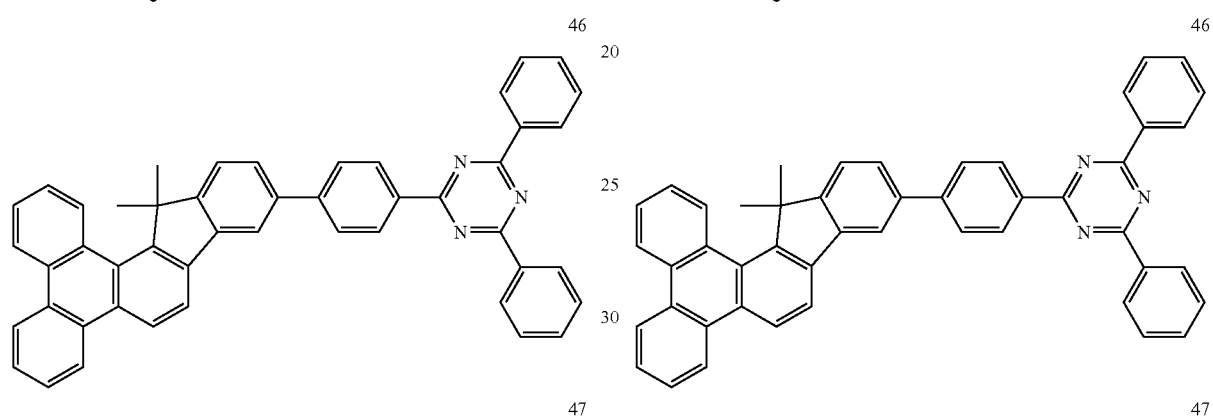
47
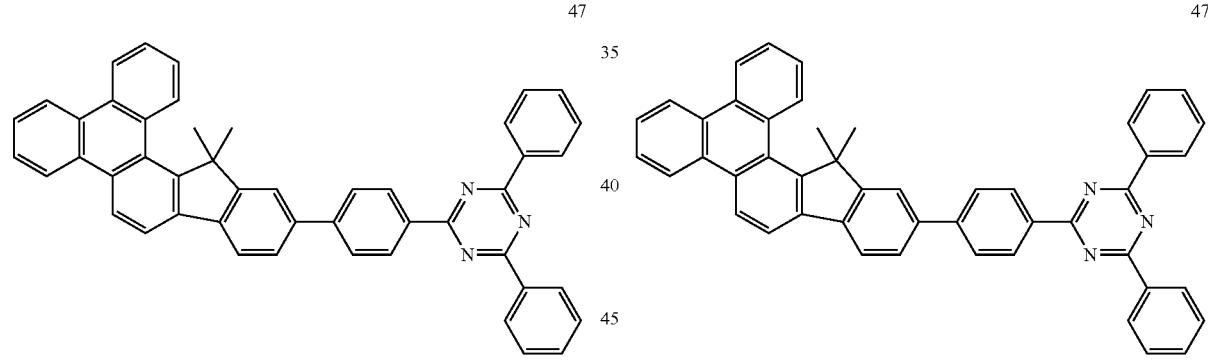
48
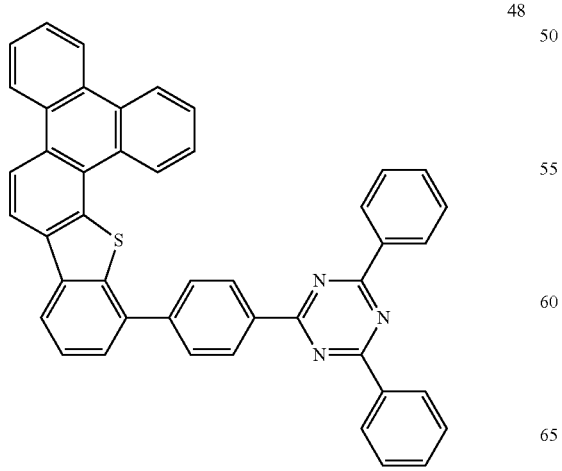
45
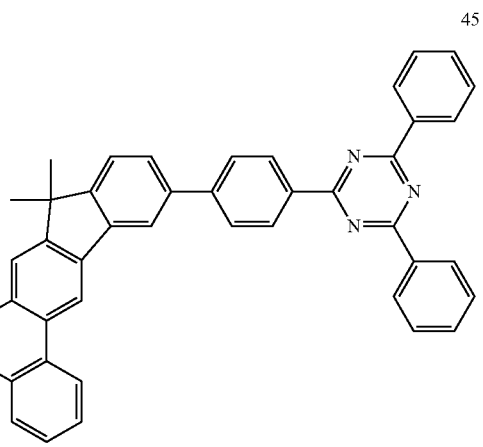
46
47
48
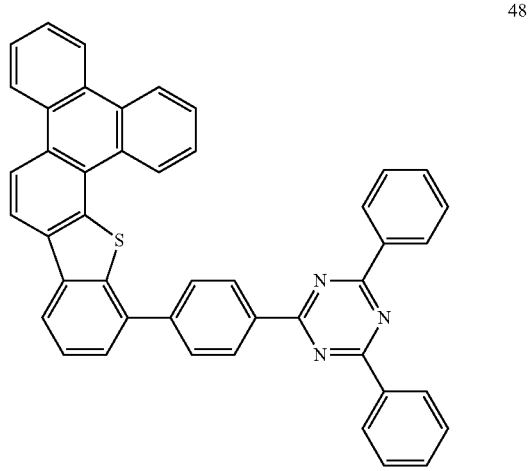

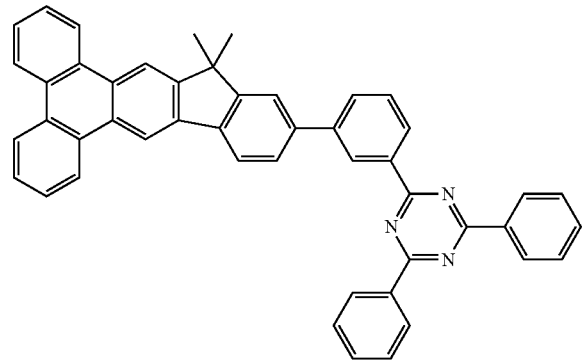
49
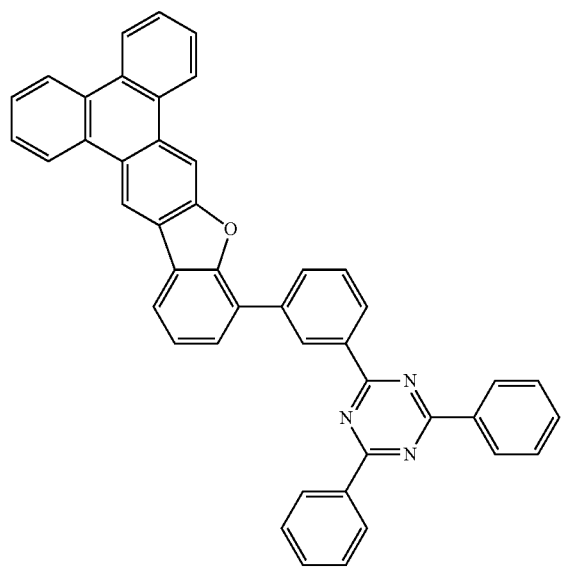
50
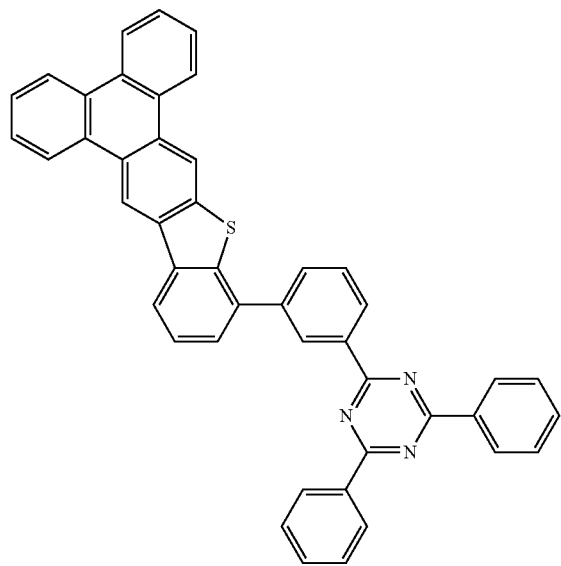
51
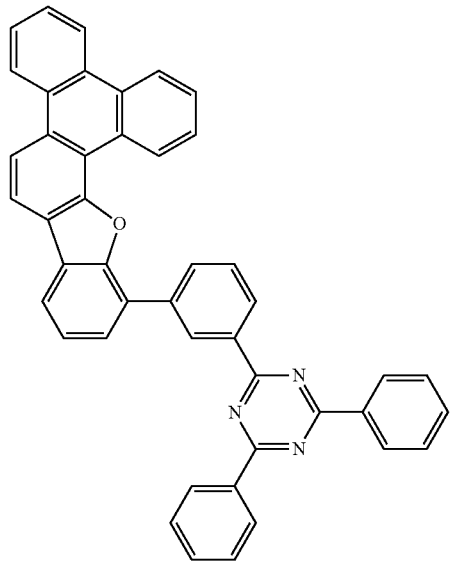
52
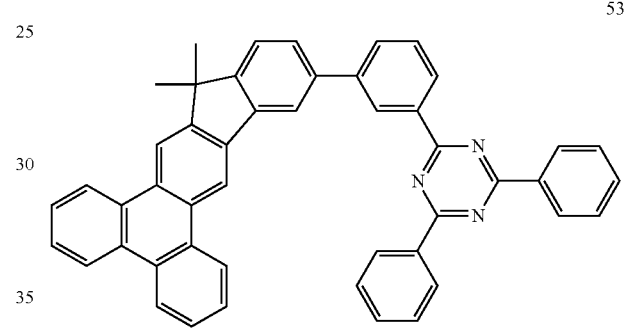
53
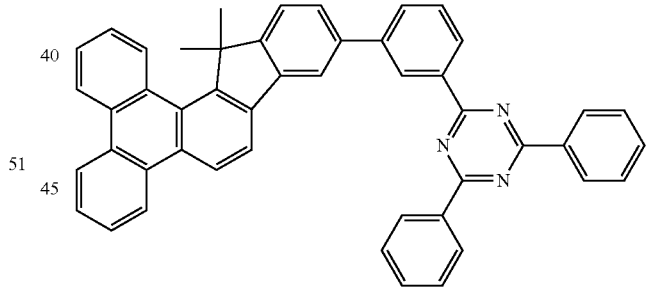
54
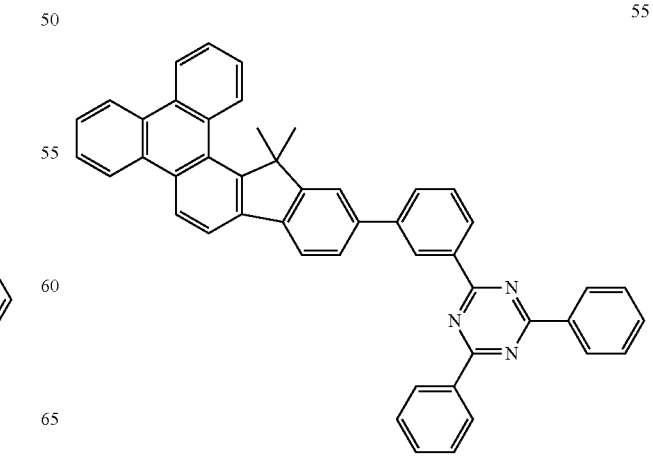
55

56
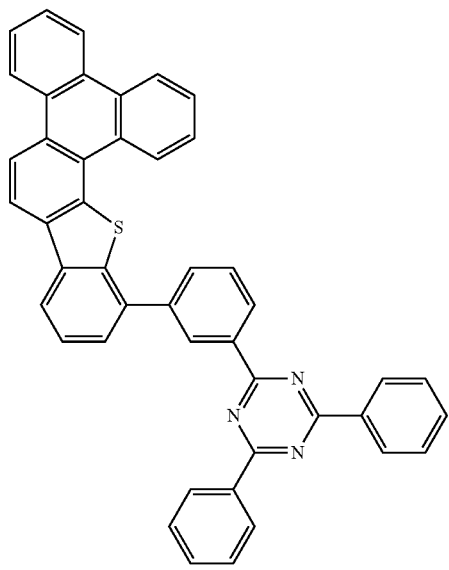
57
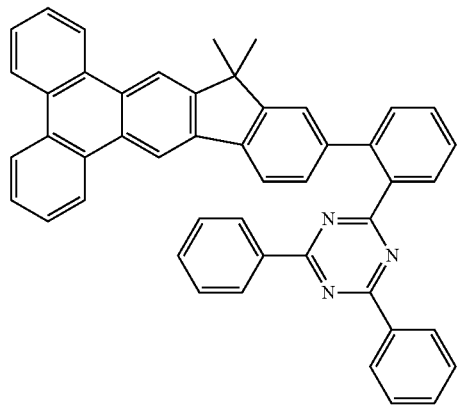
58
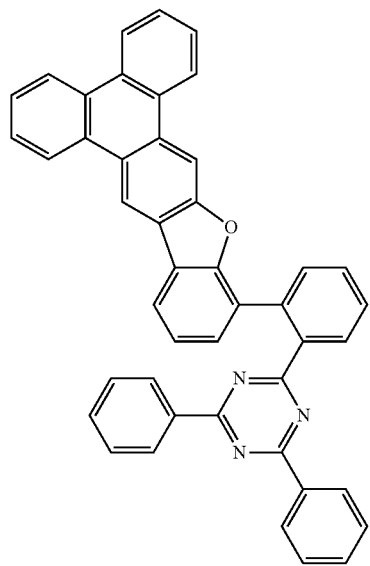
59
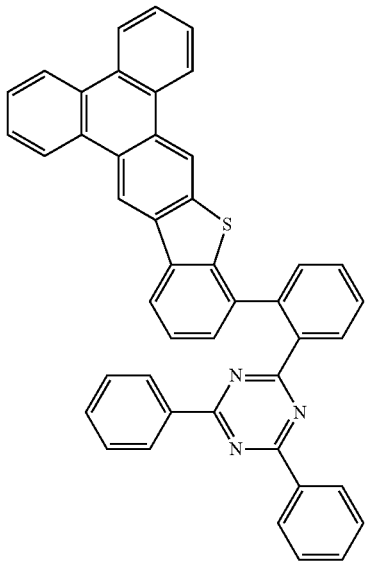
60
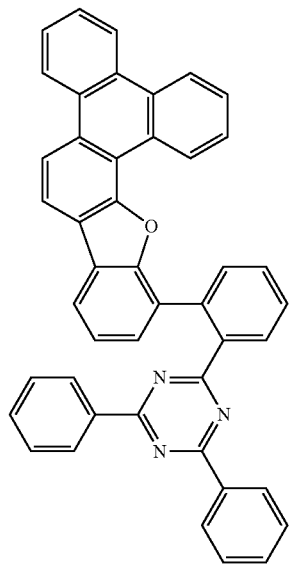
61
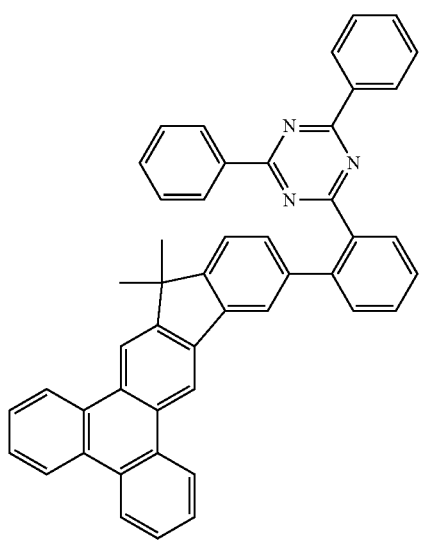

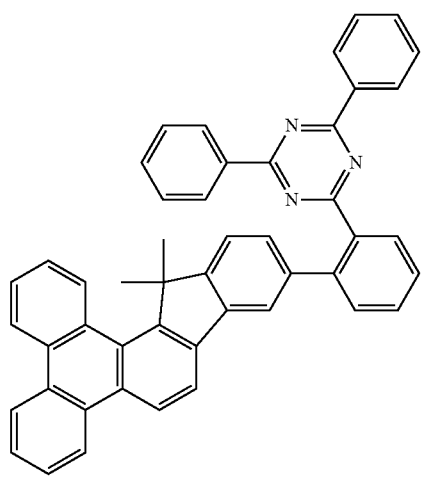
62
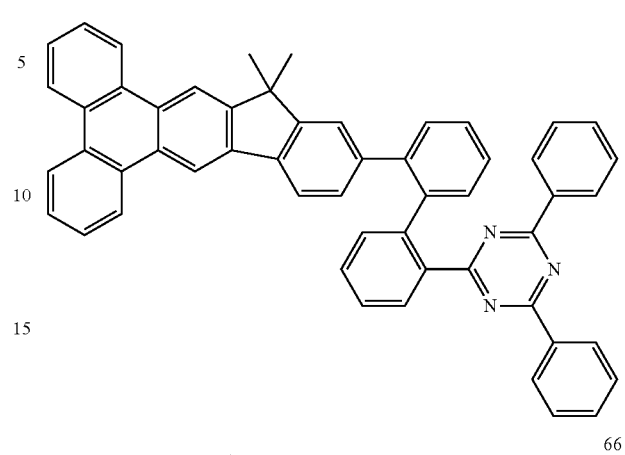
65
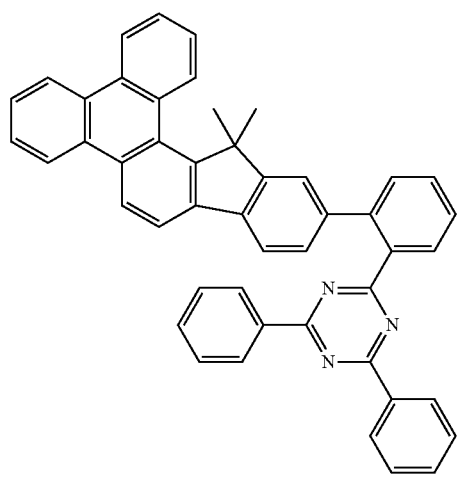
63
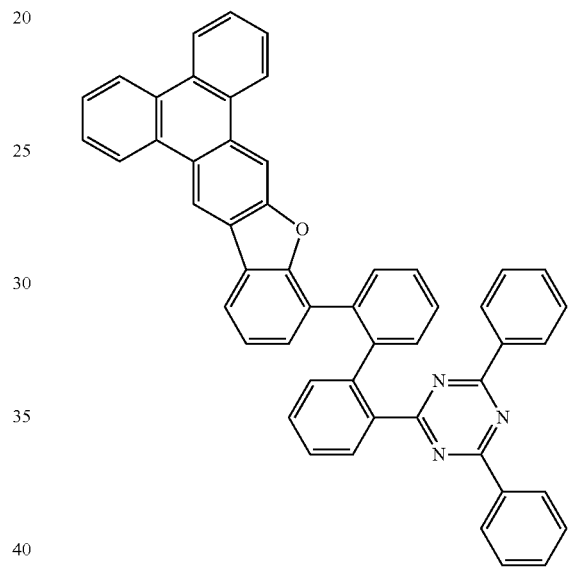
66
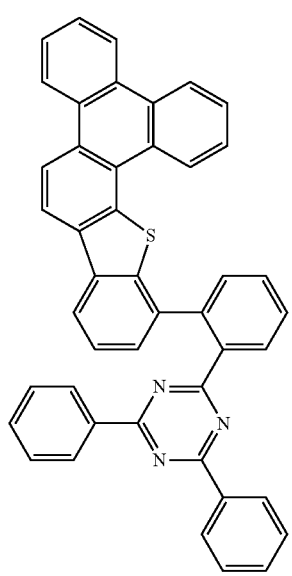
64
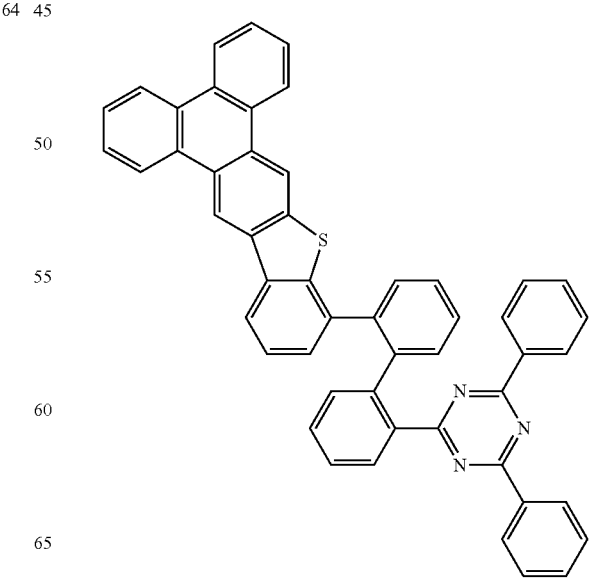
67

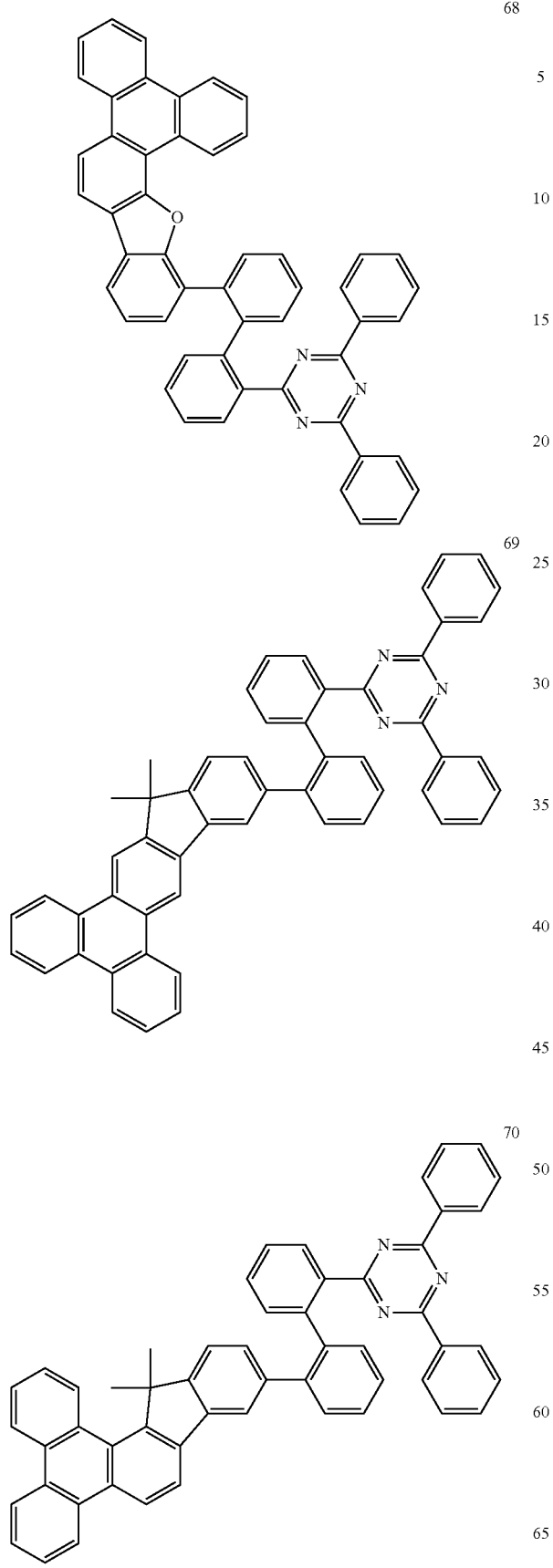

74
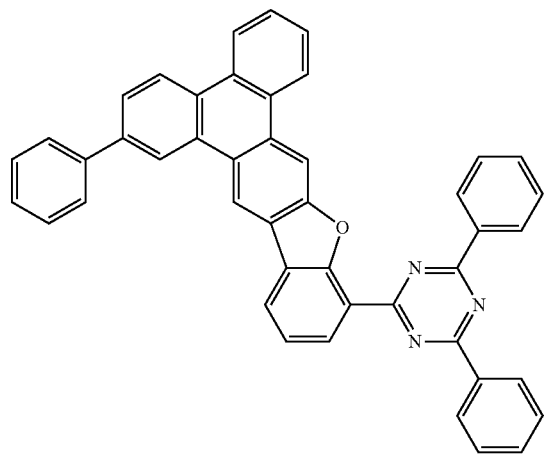
75
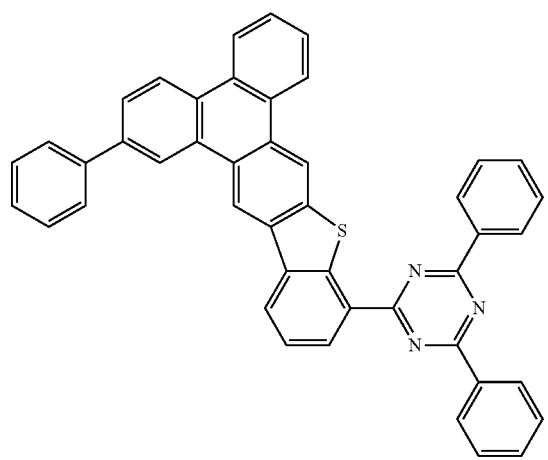
76
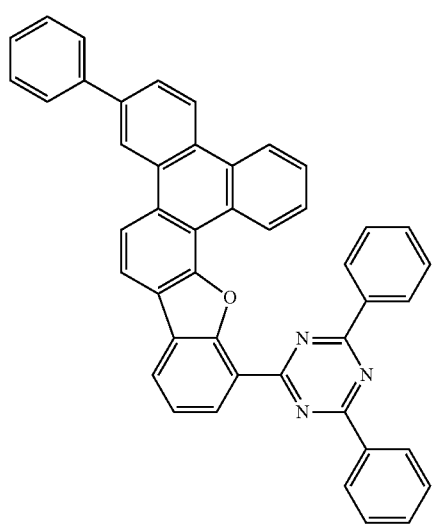
77
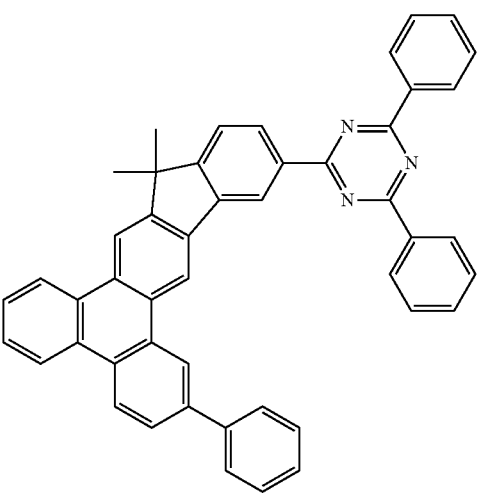
78
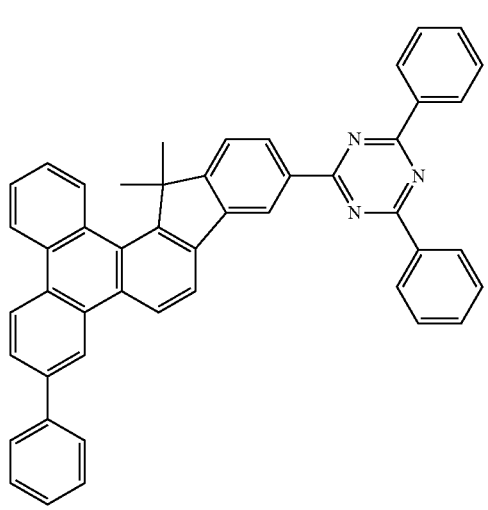
79
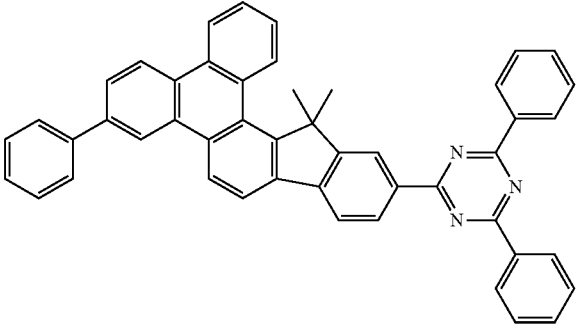

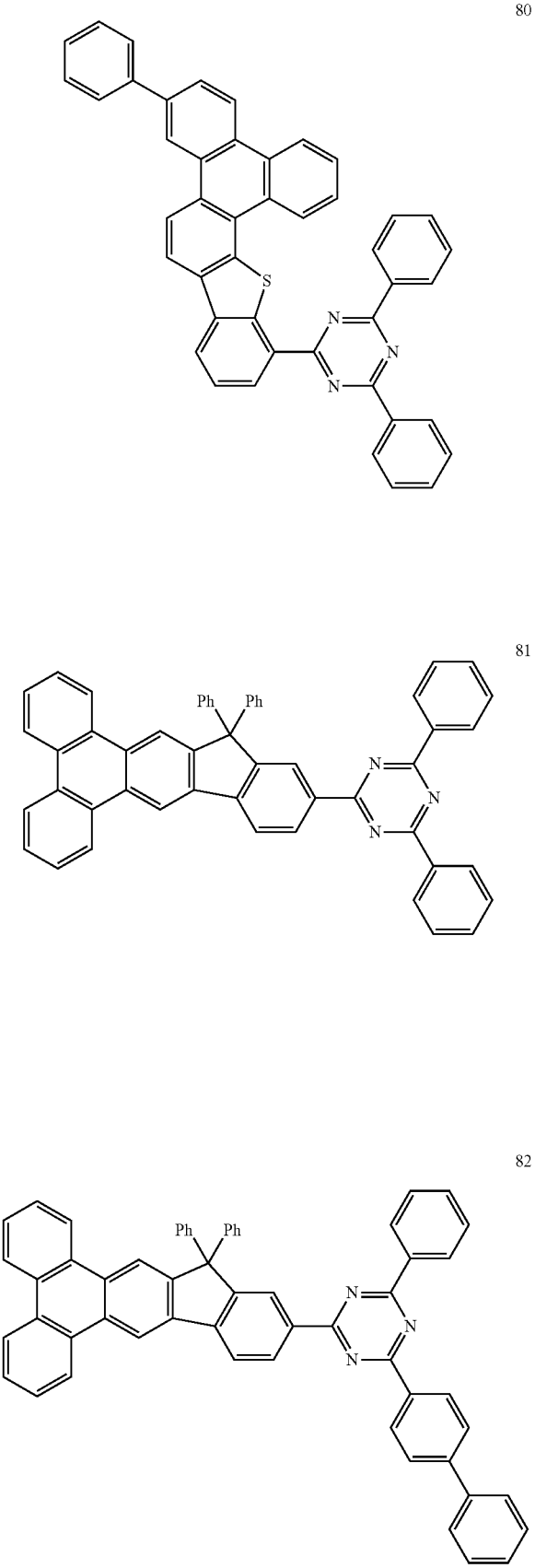
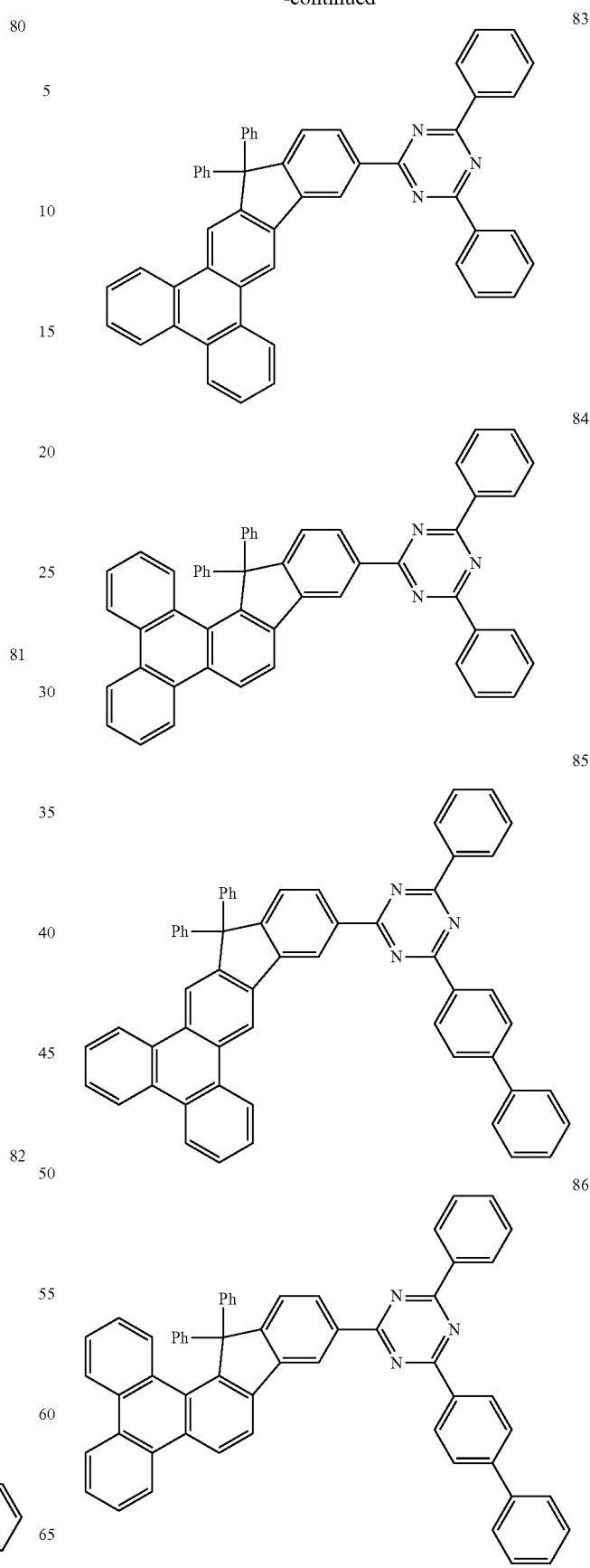

87

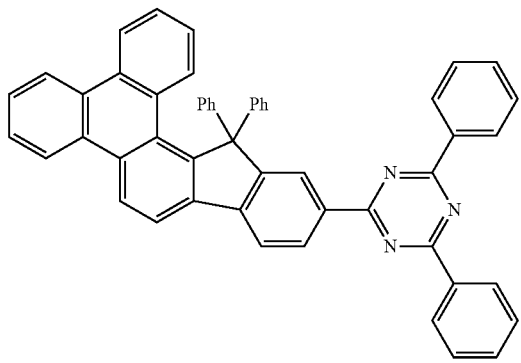

88

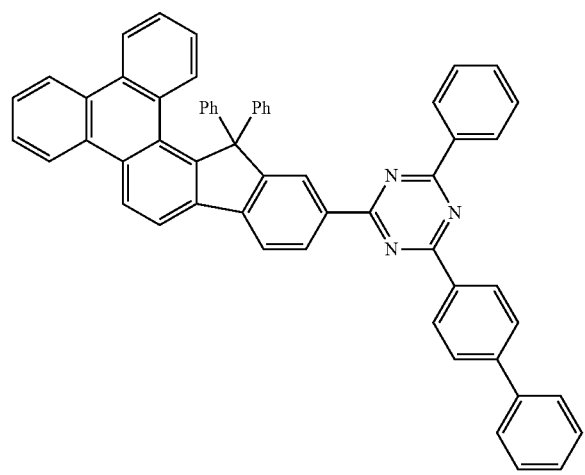

The organic compound may have LUMO energy of about −2.0 to −2.5 eV. Electron injection characteristics may increase within the LUMO energy range.

Hereinafter, an organic optoelectronic device including the organic compound is described.

The organic optoelectronic device may be any device to convert electrical energy into photoenergy and vice versa without particular limitation, and may be, for example an organic photoelectric device, an organic light emitting diode, an organic solar cell, and an organic photo-conductor drum.

Herein, an organic light emitting diode as one example of an organic optoelectronic device is described.

FIGS. 1 and 2 are cross-sectional views of an organic light emitting diode according to one embodiment.

Referring to FIG. 1, an organic optoelectronic device 100 according to one embodiment includes an anode 120 and a cathode 110 facing each other and an organic layer 105 between the anode 120 and the cathode 110.

The anode 120 may be made of a conductor having a high work function to help hole injection, for example metal, a metal oxide and/or a conductive polymer. The anode 120 may include, for example a metal or an alloy thereof such as nickel, platinum, vanadium, chromium, copper, zinc, and gold; metal oxide such as zinc oxide, indium oxide, indium tin oxide (ITO), and indium zinc oxide (IZO); a combination of a metal and an oxide such as ZnO and Al or $SnO_2$ and Sb; a conductive polymer such as poly (3-methylthiophene), poly (3,4-(ethylene-1,2-dioxy)thiophene) (PEDOT), polypyrrole, and polyaniline, but is not limited thereto.

The cathode 110 may be made of a conductor having a low work function to help electron injection, for example a metal, a metal oxide and/or a conductive polymer. The cathode 110 may include, for example a metal or an alloy thereof such as magnesium, calcium, sodium, potassium, titanium, indium, yttrium, lithium, gadolinium, aluminum silver, tin, lead, cesium, barium, and the like; a multi-layer structured material such as LiF/Al, $LiO_2$/Al, LiF/Ca, LiF/Al, and $BaF_2$/Ca, but is not limited thereto.

The organic layer 105 includes an emission layer 130 including the organic compound.

The emission layer 130 may include, for example the organic compound at alone or with at least two of the organic compounds, or as a mixture with other different compound from the organic compound. When the organic compound is mixed with the other compound, for example they may be included as a host and a dopant, wherein the organic compound may be, for example included as a host. The host may be, for example phosphorescent host or fluorescent host, for example a phosphorescent host.

When the organic compound is included as a host, the dopant may be selected from well-known inorganic, organic, organic/inorganic compound as a dopant.

Referring to FIG. 2, an organic light emitting diode 200 further includes a hole auxiliary layer 140 as well as an emission layer 130. The hole auxiliary layer 140 may further increase hole injection and/or hole mobility between the anode 120 and emission layer 130 and block electrons. The hole auxiliary layer 140 may be, for example a hole transport layer, a hole injection layer, and/or an electron blocking layer, and may include at least one layer. The organic compound may be included in the emission layer 130 and/or the hole auxiliary layer 140.

In one embodiment of the present invention, in FIG. 1 or 2, the organic layer 105 may further include an auxiliary electron transport layer, an electron transport layer, an electron injection layer, an auxiliary hole transport layer, a hole injection layer, and the like. The organic compound may be included in an emission layer 130 and/or a hole auxiliary layer 140, or may be included in an auxiliary electron transport layer, an electron transport layer, an electron injection layer, an auxiliary hole transport layer and/or a hole injection layer.

The organic light emitting diodes 100 and 200 may be manufactured by forming an anode or a cathode on a substrate, forming an organic layer in accordance with a dry coating method such as evaporation, sputtering, plasma plating, and ion plating; or a wet coating method such as spin coating, slit coating, dipping, flow coating and inkjet printing; and forming a cathode or an anode thereon.

The organic light emitting diode may be applied to an organic light emitting diode (OLED) display.

MODE FOR INVENTION

Hereinafter, the embodiments are illustrated in more detail with reference to examples. These examples, however, are not in any sense to be interpreted as limiting the scope of the invention.

Synthesis of Intermediate

Synthesis Example 1: Synthesis of Intermediate I-1

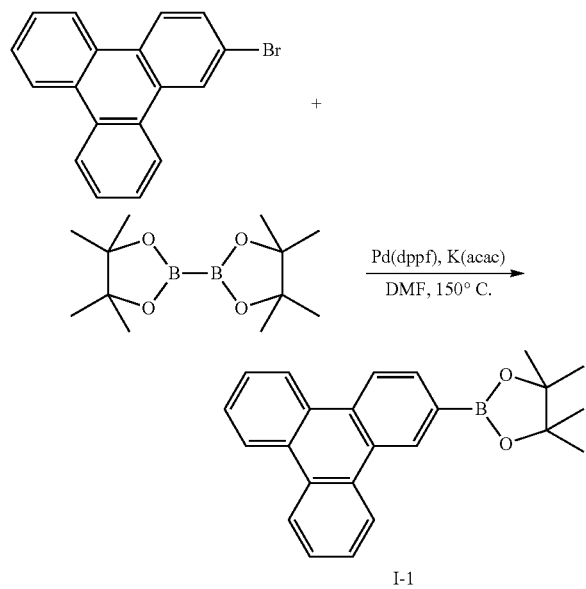

I-1

100 g (326 mmol) of 2-bromotriphenylene was dissolved in 1,000 mL of dimethyl formamide (DMF) in an environment nitrogen, 99.2 g (391 mmol) of bis(pinacolato)diboron and 1,1'-2.66 g (3.26 mmol) of bis(diphenylphosphine) ferrocene)dichloropalladium (II), and 80 g (815 mmol) of potassium acetate were added thereto, and the mixture was heated and refluxed at 150° C. for 5 hours. When the reaction was complete, water was added to the reaction solution, and the mixture was filtered and dried in a vacuum oven. The obtained residue was separated through flash column chromatography and purified, obtaining 113 g (98%) of a compound I-1.

HRMS (70 eV, EI+); m/z calcd for C24H23BO2: 354.1791. found: 354.

Elemental Analysis: C, 81%; H, 7%

Synthesis Example 2: Synthesis of Intermediate I-2

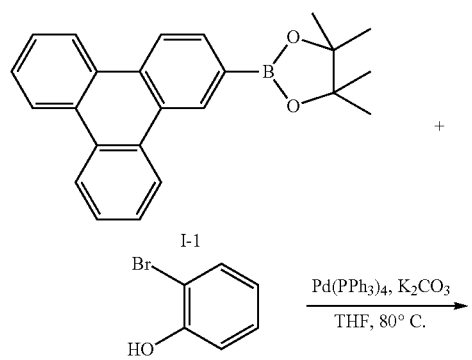

I-2

100 g (282 mmol) of the compound I-1 was dissolved in 800 mL of tetrahydrofuran (THF) in a nitrogen environment, 58.5 g (338 mmol) of 2-bromophenol and 3.26 g (2.82 mmol) of tetrakis(triphenylphosphine)palladium were added thereto, and the mixture was agitated. Then, 97.4 g (705 mmol) of potassium carbonate saturated in water was added thereto, and the obtained mixture was heated and refluxed at 80° C. for 12 hours. When the reaction was complete, water was added to the reaction solution, the mixture was extracted with dichloromethane (DCM), anhydrous MgSO4 was used to remove moisture therefrom, and the residue was filtered and concentrated under a reduced pressure. The obtained residue was separated and purified through flash column chromatography, obtaining 77.7 g (86%) of a compound I-2.

HRMS (70 eV, EI+): m/z calcd for C24H16O: 320.1201. found: 320.

Elemental Analysis: C, 90%; H, 5%

Synthesis Example 3: Synthesis of Intermediate I-3

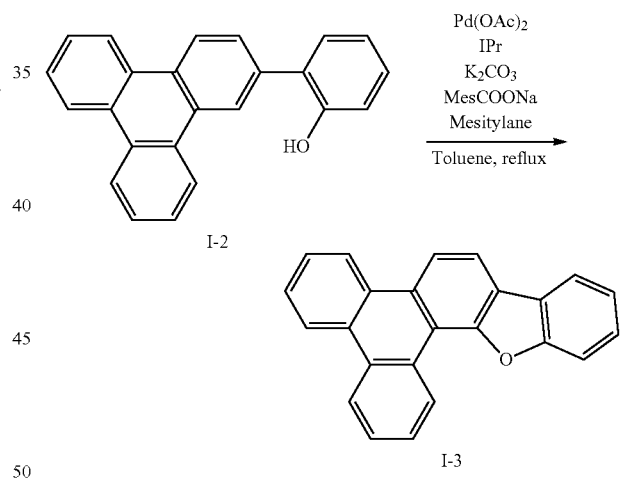

I-3

75 g (234 mmol) of the compound I-2 was dissolved in 800 mL of toluene in an air environment, 2.63 g (11.7 mmol) of palladium (II) acetate, 9.09 g (23.4 mmol) of 1,3-bis(2, 6-diisopropylphenyl)-1,3-dihydro-2H-imidazol-2-ylidene) (IPr), 4.26 g (23.4 mmol) of 4,5-diazafluoren-9-one, 21.8 g (117 mmol) of sodium 2,4,6-trimethylbenzoate, 64.7 g (468 mmol) of potassium carbonate, 200 mg of MS 3A purchased from Acros, and 1 mL of mesitylene were sequentially added thereto, and the mixture was heated and refluxed at 120° C. for 24 hours. When the reaction was complete, dichloromethane (DCM) was used for extraction, anhydrous MgSO4 was used to remove moisture therefrom, and the residue was filtered and concentrated under a reduced pressure. The obtained residue was separated and purified through flash column chromatography obtaining 35.8 g (48%) of a compound I-3.

HRMS (70 eV, EI+): m/z calcd for C24H14O: 318.1045. found: 318.

Elemental Analysis: C, 91%; H, 4%

Synthesis Example 4: Synthesis of Intermediate I-4

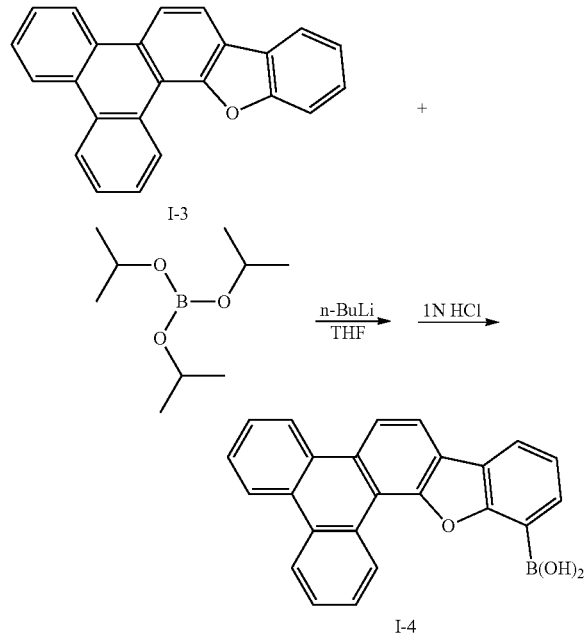

30 g (94.2 mmol) of the compound I-3 was dissolved in 300 mL of tetrahydrofuran (THF) in a nitrogen environment, and the solution was cooled down to −78° C. Then, 57 mL (141 mmol) of 2.5 M n-BuLi dissolved in hexane was slowly added thereto in a dropwise fashion over 10 minutes. The mixture was agitated at room temperature for 18 hours. When the reaction was complete, 141 mL (141 mmol) of 1N HCl was added thereto to neutralize the reaction solution. The resultant was extracted with ethylacetate (EA), anhydrous MgSO4 was used to remove moisture therefrom, and the obtained residue was washed with hexane and dichloromethane (DCM) to remove impurities, obtaining 27.0 g (79%) of a compound I-4.

HRMS (70 eV, EI+): m/z calcd for C24H15BO3: 362.1114. found: 362.

Elemental Analysis: C, 80%; H, 4%

Synthesis Example 5: Synthesis of Intermediate I-5

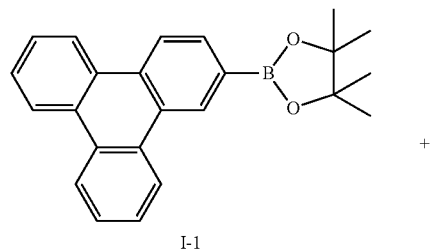

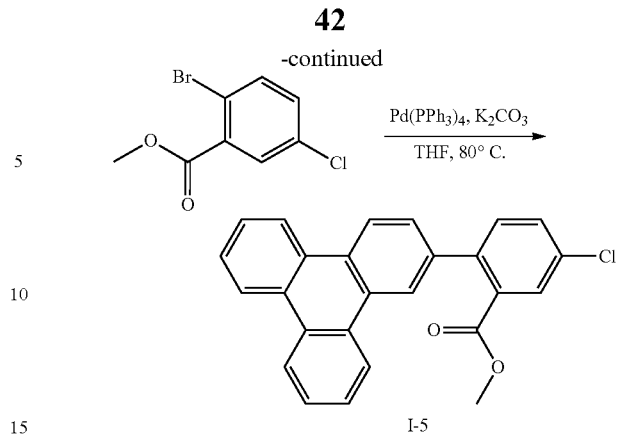

100 g (282 mmol) of the compound I-1 was dissolved in 900 mL of tetrahydrofuran (THF) in a nitrogen environment, 77.4 g (310 mmol) of methyl 2-bromo-5-chlorobenzoate and 3.26 g (2.82 mmol) of tetrakis(triphenylphosphine)palladium were added thereto, and the mixture was agitated. Then, 97.4 g (705 mmol) of potassium carbonate saturated in water was added thereto, and the mixture was heated and refluxed at 80° C. for 21 hours. When the reaction was complete, water was added to the reaction solution, dichloromethane (DCM) was used for extraction, anhydrous MgSO4 was used to remove moisture therefrom, and the residue was filtered and concentrated under a reduced pressure. This obtained residue was separated and purified through flash column chromatography, obtaining 112 g (94%) of a compound I-5.

HRMS (70 eV, EI+): m/z calcd for C26H17ClO2: 396.0917. found: 396. Elemental Analysis: C, 79%; H, 4%.

Synthesis Example 6: Synthesis of Intermediate I-6

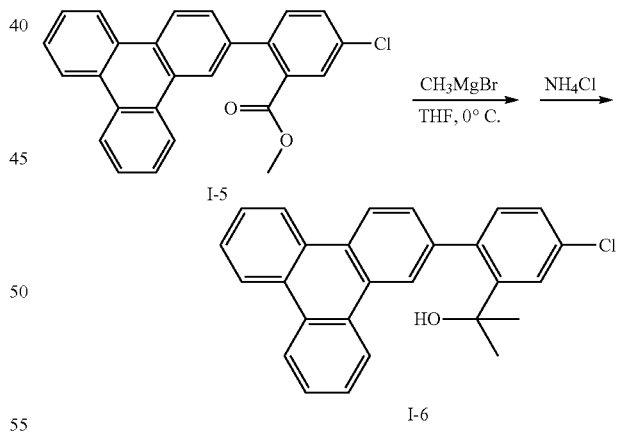

110 g (277 mmol) of the compound I-5 was dissolved in 1,100 mL of tetrahydrofuran (THF) in a nitrogen environment, and the solution was cooled down to 0° C. Then, 231 mL (693 mmol) of 3.0 M methyl magnesium bromide dissolved in dimethylether was slowly added thereto in a dropwise fashion over one hour. Then, the mixture was agitated at room temperature for 17 hours. When the reaction was complete, 44.5 g (831 mmol) of ammonium chloride dissolved in 450 mL of water was added thereto to neutralize the reaction solution. Subsequently, dichloromethane (DCM) was used for extraction, anhydrous MgSO4 was used to remove moisture therefrom, and the residue was filtered and concentrated under a reduced pressure, obtaining 109 g (99%) of a compound I-6.

HRMS (70 eV, EI+): m/z calcd for C27H21ClO: 396.1281. found: 396.

Elemental Analysis: C, 82%; H, 5%

Synthesis Example 7: Synthesis of Intermediate I-7

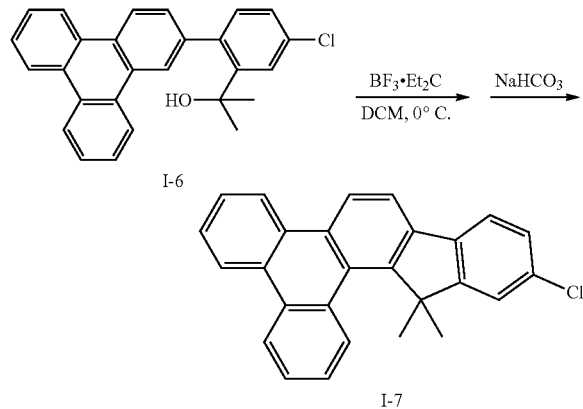

105 g (265 mmol) of the compound I-6 was dissolved in 1,300 mL of dichloromethane (DCM) in a nitrogen environment, and the solution was cooled down to 0° C. Then, 56.4 g (398 mmol) of boron trifluoride dissolved in diethyl etherate was slowly added thereto in a dropwise fashion over one hour. The obtained mixture was agitated at room temperature for 5 hours. When the reaction was complete, 33.4 g (398 mmol) of sodium bicarbonate dissolved in 0.1 L of water was added thereto to neutralize the reaction solution. Then, dichloromethane (DCM) was used for extraction, anhydrous MgSO4 was used to remove moisture therefrom, and the obtained residue was separated and purified through flash column chromatography, obtaining 73.3 g (73%) of a compound I-7.

HRMS (70 eV, EI+): m/z calcd for C27H19Cl: 378.1175. found: 378.

Elemental Analysis: C, 86%; H, 5%

Synthesis Example 8: Synthesis of Intermediate I-8

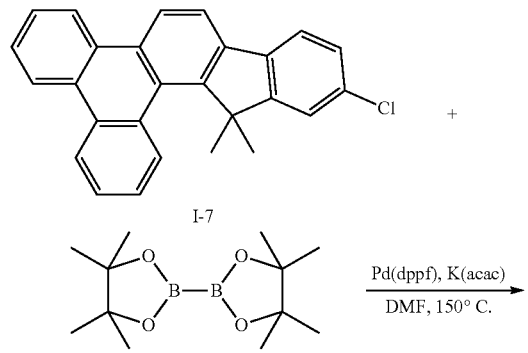

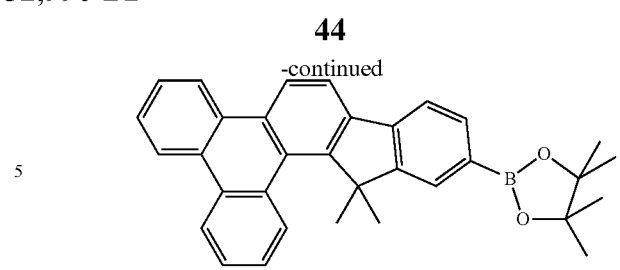

70 g (185 mmol) of the compound I-7 was dissolved in 600 mL of dimethyl formamide (DMF) in a nitrogen environment, 56.3 g (222 mmol) of bis(pinacolato)diboron, 1.51 g (1.85 mmol) of 1,1'-bis(diphenylphosphine)ferrocene)dichloropalladium (II), and 54.5 g (555 mmol) of potassium acetate were added thereto, and the mixture was heated and refluxed at 150° C. for 80 hours. When the reaction was complete, water was added to the reaction solution, and the mixture was filtered and dried in a vacuum oven. The obtained residue was separated and purified through flash column chromatography, obtaining 74.0 g (85%) of a compound I-8.

HRMS (70 eV, EI+): m/z calcd for C33H31BO2: 470.2417. found: 470.

Elemental Analysis: C, 84%; H, 7%

Synthesis Example 9: Synthesis of Intermediate I-9

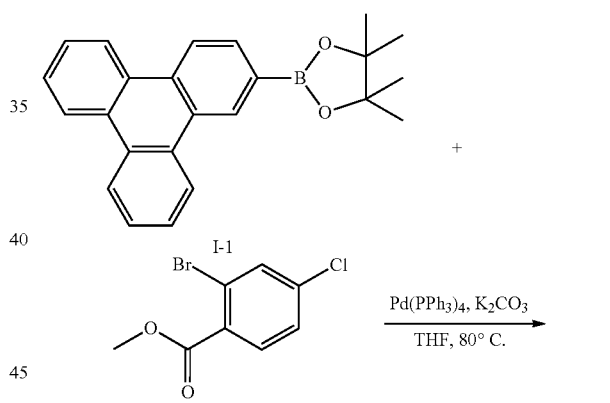

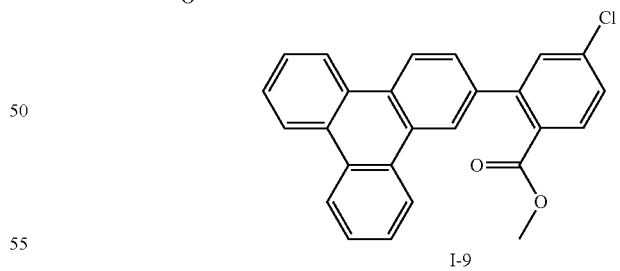

100 g (282 mmol) of the compound I-1 was dissolved in 900 mL of tetrahydrofuran (THF) in a nitrogen environment, 77.4 g (310 mmol) of methyl 2-bromo-4-chlorobenzoate and 3.26 g (2.82 mmol) of tetrakis(triphenylphosphine)palladium were added thereto, and the mixture was agitated. Then, 97.4 g (705 mmol) of potassium carbonate saturated in water was added thereto, and the mixture was heated and refluxed at 80° C. for 24 hours. When the reaction was complete, water was added to the reaction solution, dichloromethane (DCM) was used for extraction, anhydrous MgSO4 was used to remove moisture therefrom, and the residue was filtered and concentrated under a reduced pressure. This obtained residue was separated and purified through flash column chromatography, obtaining 101 g (90%) of a compound I-9.

HRMS (70 eV, EI+): m/z calcd for C26H17ClO2: 396.0917. found: 396.

Elemental Analysis: C, 79%; H, 4%

Synthesis Example 10: Synthesis of Intermediate I-10

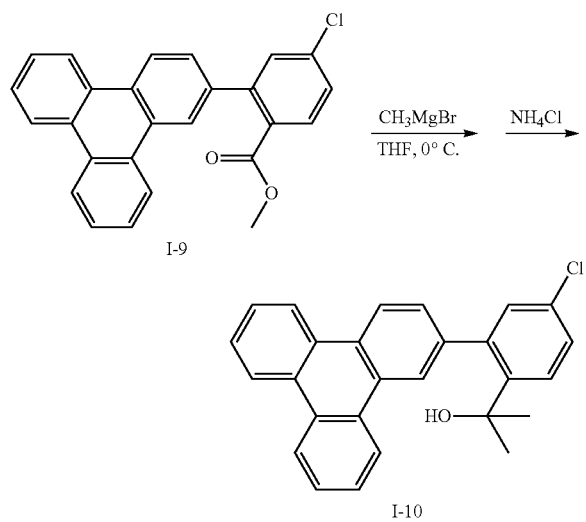

100 g (252 mmol) of the compound I-9 was dissolved in 1,000 mL of tetrahydrofuran (THF) in a nitrogen environment, and the solution was cooled down to 0° C. Then, 210 mL (630 mmol) of 3.0 M methyl magnesium bromide dissolved in diethylether was slowly added thereto in a dropwise fashion over one hour. The mixture was agitated at room temperature for 20 hours. When the reaction was complete, 40.4 g (756 mmol) of ammonium chloride dissolved in 400 mL of water was added thereto to neutralize the reaction solution. Then, dichloromethane (DCM) was used for extraction, anhydrous MgSO4 was used to remove moisture therefrom, and the residue was filtered and concentrated under a reduced pressure, obtaining 109 g (99%) of a compound I-6.

HRMS (70 eV, EI+): m/z calcd for C27H21ClO: 396.1281. found: 396.

Elemental Analysis: C, 82%; H, 5%

Synthesis Example 11: Synthesis of Intermediate I-11

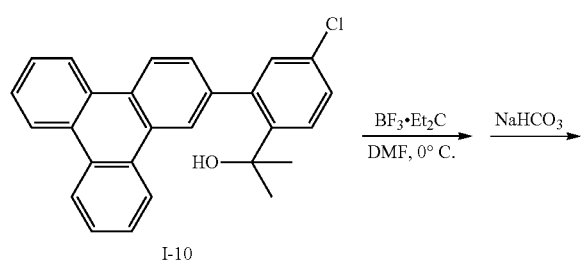

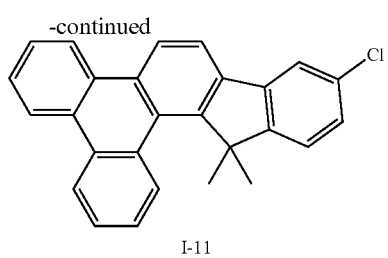

105 g (265 mmol) of the compound I-10 was dissolved in 1,300 mL of dichloromethane (DCM) in a nitrogen environment, and the solution was cooled down to 0° C. Then, 56.4 g (398 mmol) of borontrifluoride dissolved in diethyl etherate was slowly added thereto in a dropwise fashion over one hour. The mixture was agitated at room temperature for 7 hours. When the reaction was complete, 33.4 g (398 mmol) of sodium bicarbonate dissolved in 0.1 L of water was added thereto to neutralize the reaction solution. Then, dichloromethane (DCM) was used for extraction, anhydrous MgSO4 was used to remove moisture therefrom, and the obtained residue was separated and purified through flash column chromatography, obtaining 79.3 g (79%) of a compound I-11.

HRMS (70 eV, EI+): m/z calcd for C27H19Cl: 378.1175. found: 378.

Elemental Analysis: C, 86%; H, 5%

Synthesis Example 12: Synthesis of Intermediate I-12

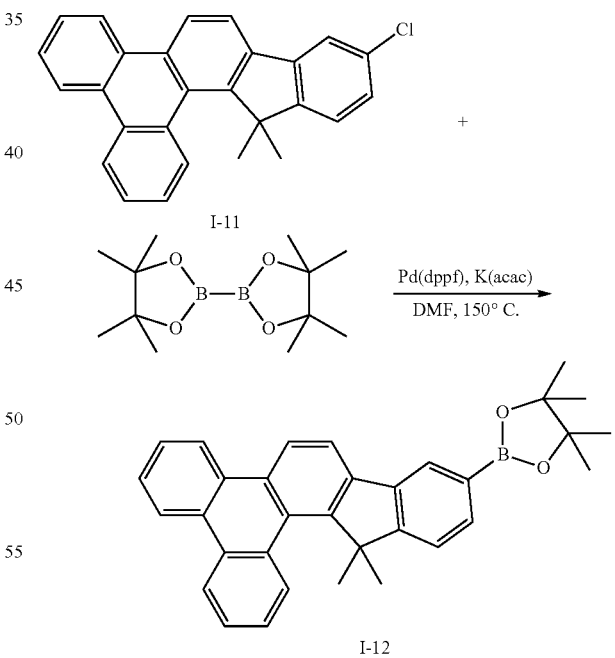

70 g (185 mmol) of the compound I-11 was dissolved in 600 mL of dimethyl formamide (DMF) in a nitrogen environment, 56.3 g (222 mmol) of bis(pinacolato)diboron, 1.51 g (1.85 mmol) of 1,1'-bis(diphenylphosphine)ferrocene)dichloropalladium (II), and 54.5 g (555 mmol) of potassium acetate were added thereto, and the mixture was heated and refluxed at 150° C. for 68 hours. When the reaction was complete, water was added to the reaction solution, and the mixture was filtered and dried in a vacuum oven. This obtained residue was separated and purified through flash column chromatography, obtaining 71.4 g (82%) of a compound I-12.

HRMS (70 eV, EI+): m/z calcd for C33H31 BO2: 470.2417. found: 470.

Elemental Analysis: C, 84%; H, 7%

Synthesis Example 13: Synthesis of Intermediate I-13

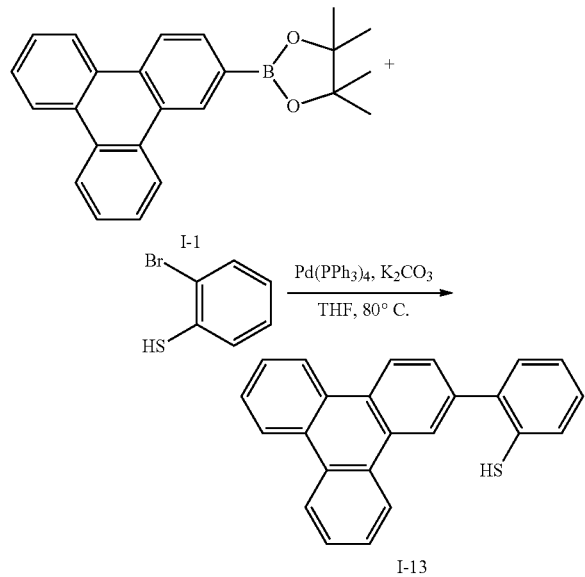

100 g (282 mmol) of the compound I-1 was dissolved in 800 mL of tetrahydrofuran (THF) in a nitrogen environment, 63.9 g (338 mmol) of 2-bromobenzenethiol and 3.26 g (2.82 mmol) of tetrakis(triphenylphosphine)palladium were added thereto, and the mixture was agitated. Then, 97.4 g (705 mmol) of potassium carbonate saturated in water was added thereto, and the mixture was heated and refluxed at 80° C. for 9 hours. When the reaction was complete, water was added to the reaction solution, dichloromethane (DCM) was used for extraction, anhydrous MgSO4 was used to remove moisture therefrom, and the residue was filtered and concentrated under a reduced pressure. This obtained residue was separated and purified through flash column chromatography, obtaining 85.4 g (90%) of a compound I-13.

HRMS (70 eV, EI+): m/z calcd for C24H16S: 336.0973. found: 336.

Elemental Analysis: C, 86%; H, 5%

Synthesis Example 14: Synthesis of Intermediate I-14

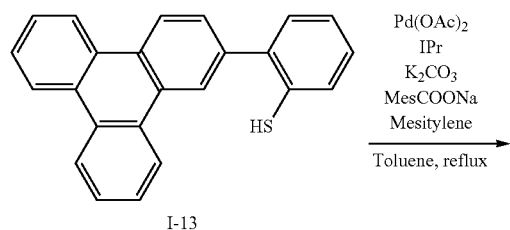

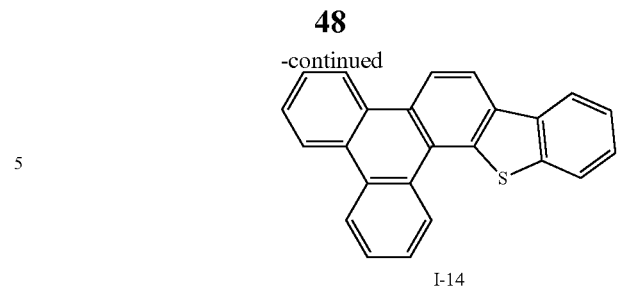

78.7 g (234 mmol) of the compound I-13 was dissolved in 800 mL of toluene in an air environment, 2.63 g (11.7 mmol) of palladium (II) acetate, 9.09 g (23.4 mmol) of 1,3-bis (2,6-diisopropylphenyl)-1,3-dihydro-2H-imidazol-2-ylidene (IPr), 4.26 g (23.4 mmol) of 4,5-diazafluoren-9-one, 21.8 g (117 mmol) of sodium 2,4,6-trimethylbenzoate, 64.7 g (468 mmol) of potassium carbonate, 200 mg of MS 3A purchased from Acros, and 1 mL of mesitylene were sequentially added thereto, and the mixture was heated and refluxed at 120° C. for 24 hour. When the reaction was complete, water was added to the reaction solution, dichloromethane (DCM) was used for extraction, anhydrous MgSO4 was used to remove moisture therefrom, and the residue was filtered and concentrated under a reduced pressure. This obtained residue was separated and purified through flash column chromatography, obtaining 33.7 g (43%) of a compound I-14.

HRMS (70 eV, EI+): m/z calcd for C24H14S: 334.0816. found: 334.

Elemental Analysis: C, 86%; H, 4%

Synthesis Example 15: Synthesis of Intermediate I-15

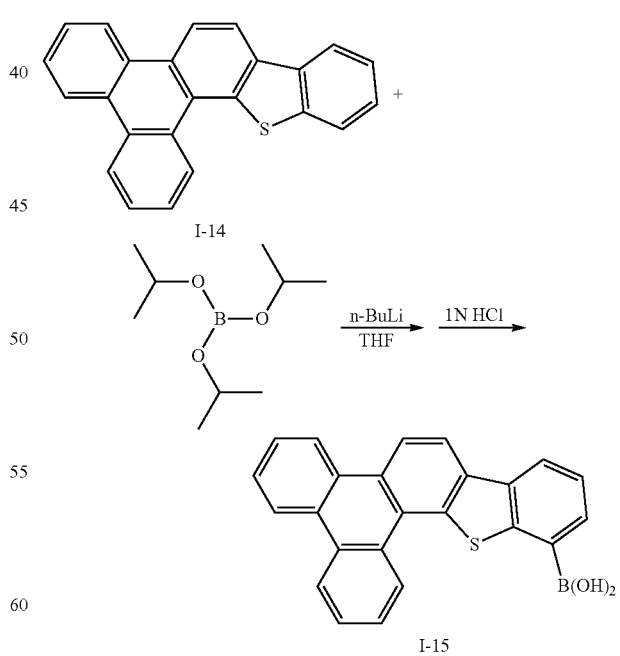

30 g (89.7 mmol) of the intermediate I-14 was dissolved in 300 mL of tetrahydrofuran (THF) in a nitrogen environment, and the solution was cooled down to −78° C. Then, 54 mL (135 mmol) of 2.5 M n-BuLi dissolved in hexane was slowly added thereto in a dropwise fashion. The mixture was agitated at room temperature for 18 hours. When the reaction was complete, 135 mL (135 mmol) of 1N HCl was added thereto to neutralize the reaction solution. The resultant was extracted with ethylacetate (EA), anhydrous MgSO4 was used to remove moisture therefrom, and the residue was washed with hexane and dichloromethane (DCM) to remove impurities, obtaining 29.2 g (86%) of a compound I-15.

HRMS (70 eV, EI+): m/z calcd for C24H15BO2S: 378.0886. found: 378.

Elemental Analysis: C, 76%; H, 4%

Synthesis Example 16: Synthesis of Intermediate I-16

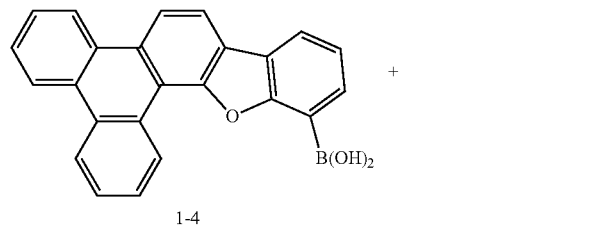

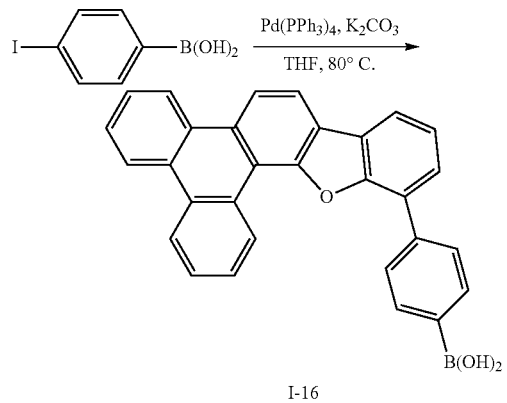

20 g (55.2 mmol) of the compound I-4 was dissolved in 180 mL of tetrahydrofuran (THF) in a nitrogen environment, 13.7 g (55.2 mmol) of 4-iodophenylboronic acid and 0.64 g (0.55 mmol) of tetrakis(triphenylphosphine) palladium were added thereto, and the mixture was agitated. Then, 19.1 g (138 mmol) of potassium carbonate was added thereto, and the mixture was heated and refluxed at 80° C. for 8 hours. When the reaction was complete, water was added to the reaction resolution, dichloromethane (DCM) was used for extraction, anhydrous MgSO4 was used to remove moisture therefrom, and the residue was filtered and concentrated under a reduced pressure. The obtained residue was separated and purified through flash column chromatography, obtaining 18.1 g (75%) of a compound I-16.

HRMS (70 eV, EI+): m/z calcd for C30H19BO3: 438.1427. found: 438.

Elemental Analysis: C, 82%; H, 4%

Synthesis Example 17: Synthesis of Intermediate I-17

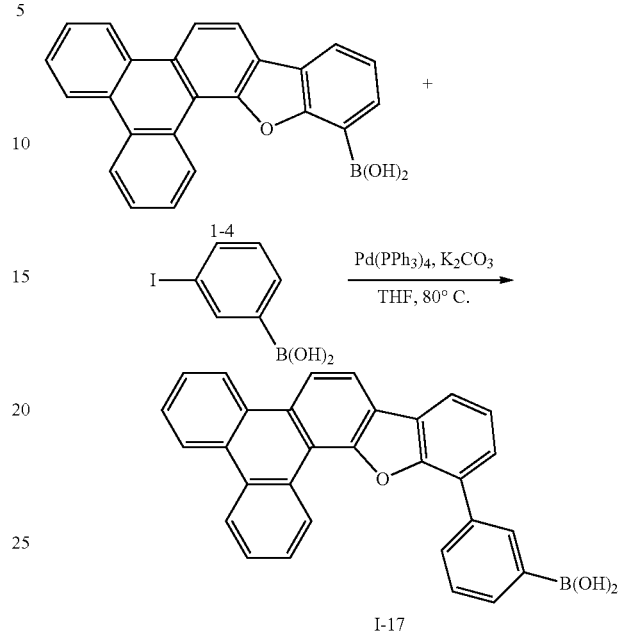

20 g (55.2 mmol) of the compound I-4 was dissolved in 180 mL of tetrahydrofuran (THF) in a nitrogen environment, 13.7 g (55.2 mmol) of 3-iodophenylboronic acid and 0.64 g (0.55 mmol) of tetrakis(triphenylphosphine)palladium were added thereto, and the mixture was agitated. Then, 19.1 g (138 mmol) of potassium carbonate saturated in water was added thereto, and the obtained mixture was heated and refluxed at 80° C. for 8 hours. When the reaction was complete, water was added to the reaction solution, dichloromethane (DCM) was used for extraction, anhydrous MgSO4 was used to remove moisture therefrom, and the residue was filtered and concentrated under a reduced pressure. The obtained residue was separated and purified through flash column chromatography, obtaining 16.5 g (68%) of a compound I-17.

HRMS (70 eV, EI+): m/z calcd for C30H19BO3: 438.1427. found: 438.

Elemental Analysis: C, 82%; H, 4%

Synthesis Example 18: Synthesis of Intermediate I-18

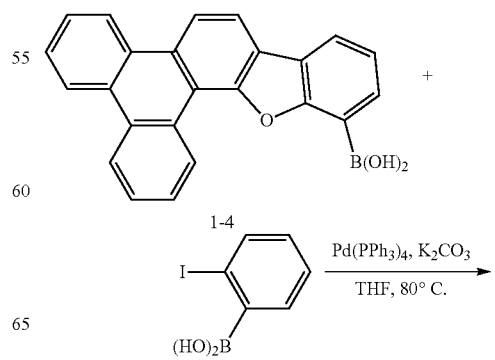

-continued

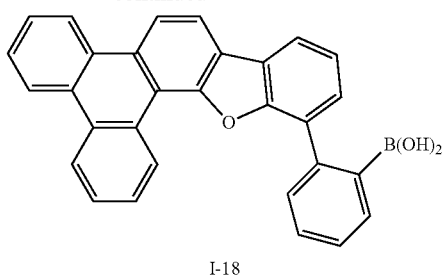

I-18

20 g (55.2 mmol) of the compound I-4 was dissolved in 180 mL of tetrahydrofuran (THF) in a nitrogen environment, 13.7 g (55.2 mmol) of 2-iodophenylboronic acid and 0.64 g (0.55 mmol) of tetrakis(triphenylphosphine)palladium were added thereto, and the mixture was agitated. Then, 19.1 g (138 mmol) of potassium carbonate saturated in water was added thereto, and the mixture was heated and refluxed at 80° C. for 10 hours. When the reaction was complete, water was added to the reaction solution, dichloromethane (DCM) was used for extraction, anhydrous MgSO4 was used to remove moisture therefrom, and the residue was filtered and concentrated under a reduced pressure. The obtained residue was separated and purified through flash column chromatography, obtaining 13.3 g (55%) of a compound I-18.

HRMS (70 eV, EI+): m/z calcd for C30H19BO3: 438.1427. found: 438.

Elemental Analysis: C, 82%; H, 4%

Synthesis of Organic Compound

Example 1: Synthesis of Compound 4

-continued

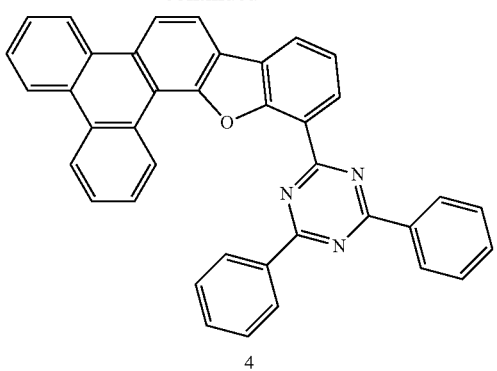

4

20 g (55.2 mmol) of the compound 1-4 was dissolved in 200 mL of tetrahydrofuran (THF) in a nitrogen environment, 14.8 g (55.2 mmol) of 2-chloro-4,6-diphenyl-1,3,5-triazine and 0.64 g (0.55 mmol) of tetrakis(triphenylphosphine) palladium were added thereto, and the mixture was agitated. Then, 19.1 g (138 mmol) of potassium carbonate saturated in water was added thereto, and the mixture was heated and refluxed at 80° C. for 17 hours. When the reaction was complete, water was added to the reaction solution, dichloromethane (DCM) was used for extraction, anhydrous MgSO4 was used to remove moisture therefrom, and the residue was filtered and concentrated under a reduced pressure. The obtained residue was separated and purified through flash column chromatography, obtaining 24.6 g (81%) of a compound 4.

HRMS (70 eV, EI+): m/z calcd for C39H23N3O: 549.1841. found: 549.

Elemental Analysis: C, 85%; H, 4%

Example 2: Synthesis of Compound 6

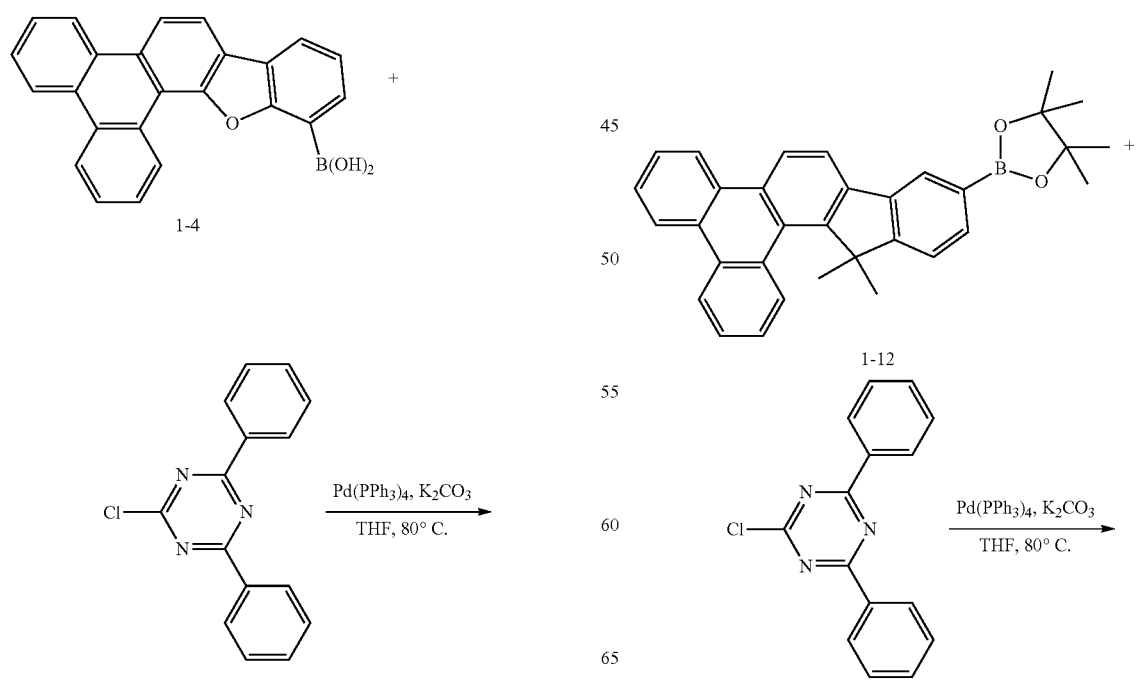

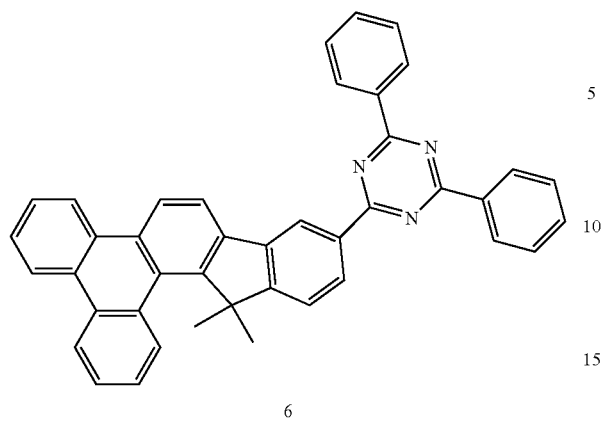

6

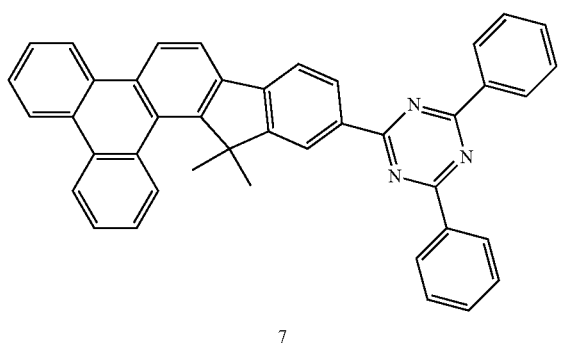

7

20 g (42.5 mmol) of the compound I-12 was dissolved in 160 mL of tetrahydrofuran (THF) in a nitrogen environment, 11.4 g (42.5 mmol) of 2-chloro-4,6-diphenyl-1,3,5-triazine and 0.49 g (0.43 mmol) of tetrakis(triphenylphosphine) palladium were added thereto, and the mixture was agitated. Then, 14.7 g (106 mmol) of potassium carbonate saturated in water was added thereto, and the mixture was heated and refluxed at 80° C. for 8 hours. When the reaction was complete, water was added to the reaction solution, dichloromethane (DCM) was used for extraction, anhydrous MgSO4 was used to remove moisture therefrom, and the residue was filtered and concentrated under a reduced pressure. The obtained residue was separated and purified through flash column chromatography, obtaining 17.1 g (70%) of a compound 6.

HRMS (70 eV, EI+): m/z calcd for C42H29N3: 575.2361. found: 575.

Elemental Analysis: C, 88%; H, 5%

20 g (42.5 mmol) of the compound 1-8 was dissolved in 160 mL of tetrahydrofuran (THF) in a nitrogen environment, 11.4 g (42.5 mmol) of 2-chloro-4,6-diphenyl-1,3,5-triazine and 0.49 g (0.43 mmol) of tetrakis(triphenylphosphine) palladium were added thereto, and the mixture was agitated. Then, 14.7 g (106 mmol) of potassium carbonate saturated in water was added thereto, and the mixture was heated and refluxed at 80° C. for 10 hours. When the reaction was complete, water was added to the reaction solution, dichloromethane (DCM) was used for extraction, anhydrous MgSO4 was used to remove moisture therefrom, and the residue was filtered and concentrated under a reduced pressure. The obtained residue was separated and purified through flash column chromatography, obtaining 15.7 g (64%) of a compound 7.

HRMS (70 eV, EI+): m/z calcd for C42H29N3: 575.2361. found: 575.

Elemental Analysis: C, 88%; H, 5%

Example 3: Synthesis of Compound 7

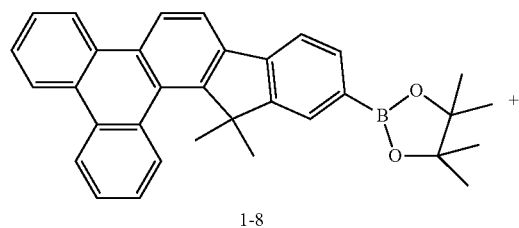

1-8

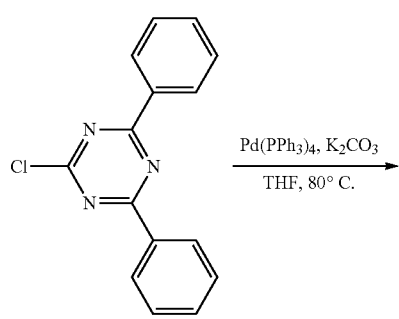

Example 4: Synthesis of Compound 8

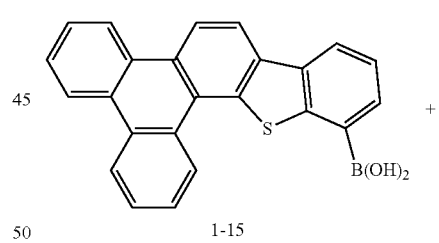

1-15

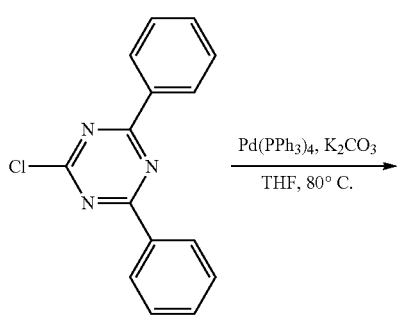

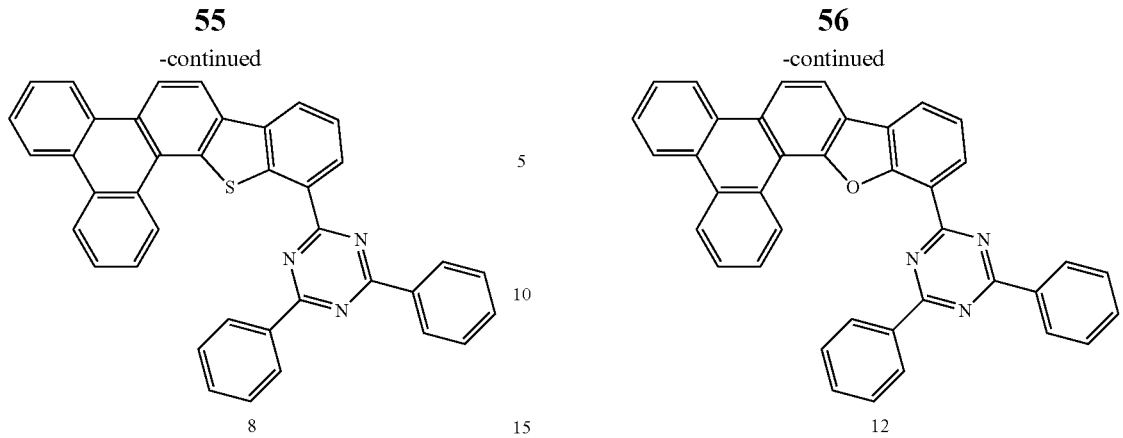

20 g (52.9 mmol) of the compound 1-15 was dissolved in 200 mL of tetrahydrofuran (THF) in a nitrogen environment, 14.2 g (52.9 mmol) of 2-chloro-4,6-diphenyl-1,3,5-triazine and 0.61 g (0.53 mmol) of tetrakis(triphenylphosphine)palladium were added thereto, and the mixture was agitated. Then, 18.3 g (132 mmol) of potassium carbonate saturated in water was added thereto, and the mixture was heated and refluxed at 80° C. for 15 hours. When the reaction was complete, water was added to the reaction solution, dichloromethane (DCM) was used for extraction, anhydrous MgSO4 was used to remove moisture therefrom, and the residue was filtered and concentrated under a reduced pressure. The obtained residue was separated and purified through flash column chromatography, obtaining 26.6 g (89%) of a compound 8.

HRMS (70 eV, EI+): m/z calcd for C39H23N3S: 565.1613. found: 565.

Elemental Analysis: C, 83%; H, 4%

20 g (52.2 mmol) of the compound 1-4 was dissolved in 200 mL of tetrahydrofuran (THF) in a nitrogen environment, 14.7 g (55.2 mmol) of 2-chloro-4,6-diphenylpyrimidine and 0.64 g (0.55 mmol) of tetrakis(triphenylphosphine)palladium were added thereto, and the mixture was agitated. Then, 19.1 g (138 mmol) of potassium carbonate saturated in water was added thereto, and the mixture was heated and refluxed at 80° C. for 20 hours. When the reaction was complete, water was added to the reaction solution, dichloromethane (DCM) was used for extraction, anhydrous MgSO4 was used to remove moisture therefrom, and the residue was filtered and concentrated under a reduced pressure. The obtained residue was separated and purified through flash column chromatography, obtaining 27.3 g (90%) of a compound 12.

HRMS (70 eV, EI+): m/z calcd for C40H24N2O: 548.1889. found: 548.

Elemental Analysis: C, 88%; H, 4%

Example 5: Synthesis of Compound 12

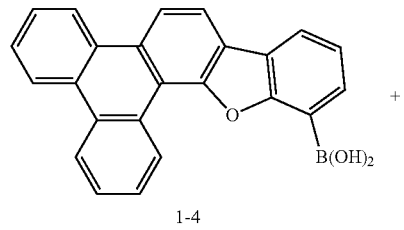

Example 6: Synthesis of Compound 20

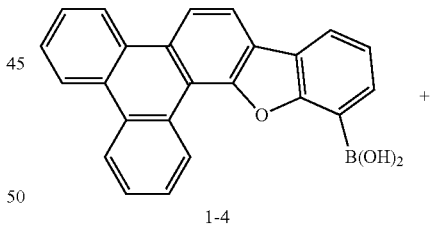

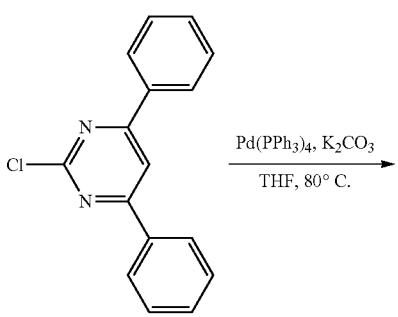

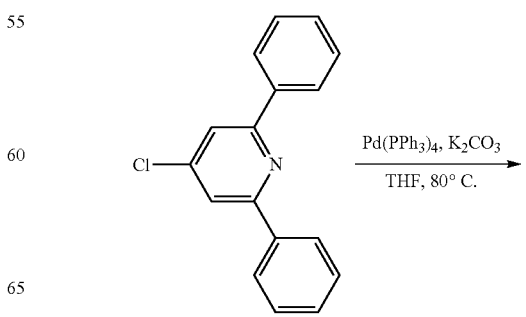

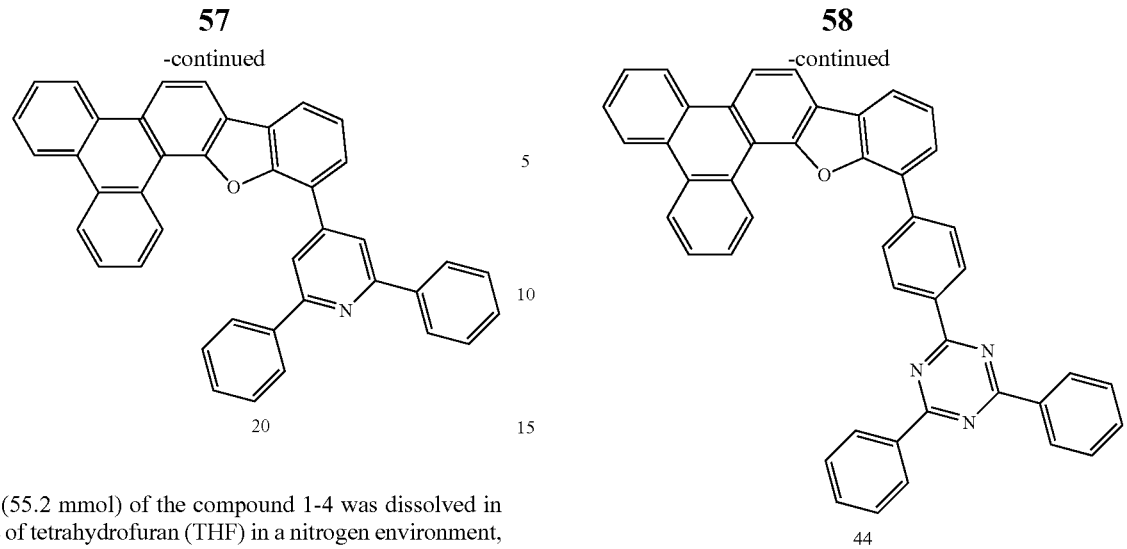

20 g (55.2 mmol) of the compound 1-4 was dissolved in 200 mL of tetrahydrofuran (THF) in a nitrogen environment, 14.7 g (55.2 mmol) of 4-chloro-2,6-diphenylpyridine and 0.64 g (0.55 mmol) of tetrakis(triphenylphosphine)palladium were added thereto, and the mixture was agitated. Then, 19.1 g (138 mmol) of potassium carbonate saturated in water was added thereto, and the mixture was heated and refluxed at 80° C. for 16 hours. When the reaction was complete, water was added to the reaction solution, dichloromethane (DCM) was used for extraction, anhydrous MgSO4 was used to remove moisture therefrom, and the residue was filtered and concentrated under a reduced pressure. The obtained residue was separated and purified through flash column chromatography, obtaining 25.4 g (84%) of a compound 20.

HRMS (70 eV, EI+): m/z calcd for C41H25NO: 547.1936. found: 547.

Elemental Analysis: C, 90%; H, 5%

Example 7: Synthesis of Compound 44

15 g (34.2 mmol) of the compound 1-16 was dissolved in 130 mL of tetrahydrofuran (THF) in a nitrogen environment, 9.16 g (34.2 mmol) of 2-chloro-4,6-diphenyl-1,3,5-triazine and 0.39 g (0.34 mmol) of tetrakis(triphenylphosphine)palladium were added thereto, and the mixture was agitated. Then, 11.8 g (85.5 mmol) of potassium carbonate saturated in water was added thereto, and the mixture was heated and refluxed at 80° C. for 10 hours. When the reaction was complete, water was added to the reaction solution, dichloromethane (DCM) was used for extraction, anhydrous MgSO4 was used to remove moisture therefrom, and the residue was filtered and concentrated under a reduced pressure. The obtained residue was separated and purified through flash column chromatography, obtaining 18.2 g (85%) of a compound 44.

HRMS (70 eV, EI+): m/z calcd for C45H27N3O: 625.2154. found: 625.

Elemental Analysis: C, 86%; H, 4%

Example 8: Synthesis of Compound 52

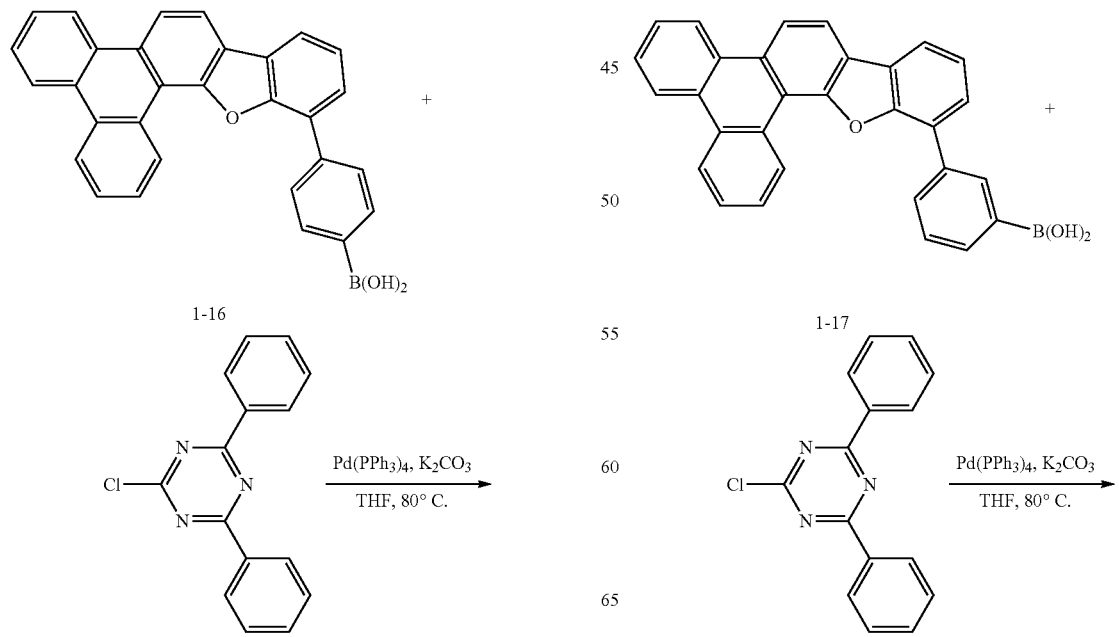

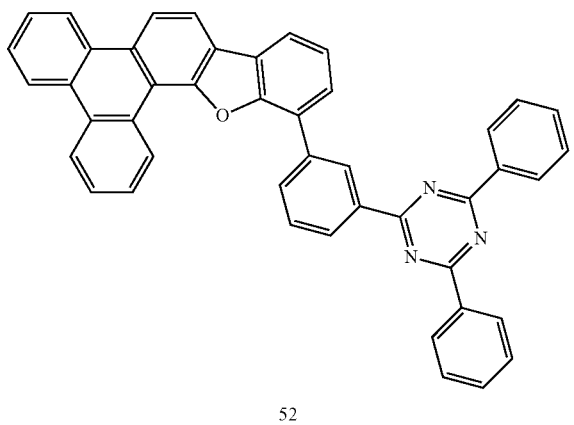

52

15 g (34.2 mmol) of the compound 1-17 was dissolved in 130 mL of tetrahydrofuran (THF) in a nitrogen environment, 9.16 g (34.2 mmol) of 2-chloro-4,6-diphenyl-1,3,5-triazine and 0.39 g (0.34 mmol) of tetrakis(triphenylphosphine) palladium were added thereto, and the mixture was agitated. Then, 11.8 g (85.5 mmol) of potassium carbonate saturated in water was added thereto, and the mixture was heated and refluxed at 80° C. for 9 hours. When the reaction was complete, water was added to the reaction solution, dichloromethane (DCM) was used for extraction, anhydrous MgSO4 was used to remove moisture therefrom, and the residue was filtered and concentrated under a reduced pressure. The obtained residue was separated and purified through flash column chromatography, obtaining 17.3 g (81%) of a compound 52.

HRMS (70 eV, EI+): m/z calcd for C45H27N3O: 625.2154. found: 625.

Elemental Analysis: C, 86%; H, 4%

Example 9: Synthesis of Compound 60

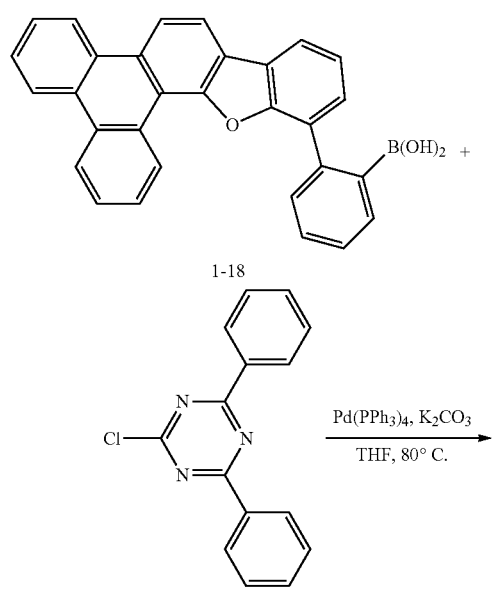

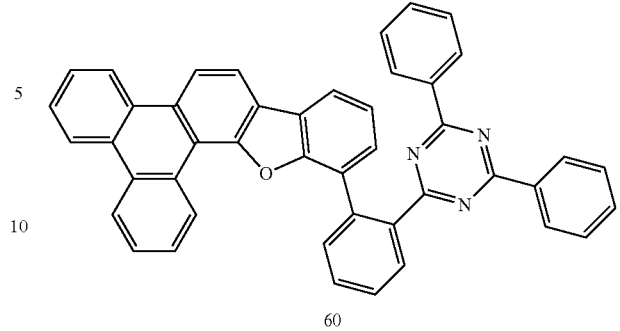

60

13 g (29.7 mmol) of the compound 1-18 was dissolved in 130 mL of tetrahydrofuran (THF) in a nitrogen environment, 7.94 g (29.7 mmol) of 2-chloro-4,6-diphenyl-1,3,5-triazine and 0.35 g (0.30 mmol) of tetrakis(triphenylphosphine) palladium were added thereto, and the mixture was agitated. Then, 10.3 g (74.3 mmol) of potassium carbonate saturated in water was added thereto, and the mixture was heated and refluxed at 80° C. for 26 hours. When the reaction was complete, water was added to the reaction solution, dichloromethane (DCM) was used for extraction, anhydrous MgSO4 was used to remove moisture therefrom, and the residue was filtered and concentrated under a reduced pressure. The obtained residue was separated and purified through flash column chromatography, obtaining 9.85 g (53%) of a compound 60.

HRMS (70 eV, EI+): m/z calcd for C45H27N3O: 625.2154. found: 625.

Elemental Analysis: C, 86%; H, 4%

Manufacture of Organic Light Emitting Diode

Example 10

The compound 4 according to Example 1 as a host and Ir(PPy)3 as a dopant were used to manufacture an organic light emitting diode. As for an anode, 1000 Å-thick ITO was used, and as for a cathode, 1000 Å-thick aluminum (Al) was used.

Specifically, illustrating a method of manufacturing an organic light emitting diode, the anode is manufactured by cutting an ITO glass substrate having 15 Ω/cm² of sheet resistance into a size of 50 mm×50 mm×0.7 mm, ultrasonic wave-cleaning them in acetone, isopropylalcohol, and pure water for 5 minutes respectively, and UV ozone cleaning them for 30 minutes.

On the substrate, an 800 Å-thick hole transport layer (HTL) was formed by depositing N4,N4'-di(naphthalen-1-yl)-N4,N4'-diphenylbiphenyl-4,4'-diamine (NPB) (80 nm) to a vacuum degree of 650×10⁻⁷ Pa at a deposition rate raging from 0.1 to 0.3 nm/s.

Subsequently, a 300 Å-thick emission layer was formed by using the compound 1 according to Example 1 under the same vacuum deposit condition, and herein, Ir(PPy)3 as a phosphorescent dopant was simultaneously deposited. Herein, the phosphorescent dopant in an amount of 7 wt % was deposited based on 100 wt % of the emission layer by adjusting the deposition rate of the phosphorescent dopant.

On the emission layer, a 50 Å-thick hole-blocking layer was formed by depositing bis(2-methyl-8-quinolinolate)-4-(phenylphenolato)aluminum (BAlq) under the same vacuum deposit condition. On the hole-blocking layer, a 200 Å-thick electron-transport layer was formed by depositing Alq3 under the same vacuum deposition condition. On the electron transport layer, a cathode was formed by sequentially depositing LiF and Al, manufacturing an organic photoelectric device.

The organic photoelectric device had a structure of ITO/ NPB (80 nm)/EML (compound 4 (93 wt %)+Ir(PPy)3 (7 wt %), 30 nm)/Balq (5 nm)/Alq3 (20 nm)/LiF (1 nm)/Al (100 nm).

Example 11

An organic light emitting diode was manufactured according to the same method as Example 10 except for using the compound 6 according to Example 2 instead of the compound 4 according to Example 1.

Example 12

An organic light emitting diode was manufactured according to the same method as Example 10 except for using the compound 7 according to Example 3 instead of the compound 4 according to Example 1.

Example 13

An organic light emitting diode was manufactured according to the same method as Example 10 except for using the compound 8 according to Example 4 instead of the compound 4 according to Example 1.

Example 14

An organic light emitting diode was manufactured according to the same method as Example 10 except for using the compound 12 according to Example 5 instead of the compound 4 according to Example 1.

Example 15

An organic light emitting diode was manufactured according to the same method as Example 10 except for using the compound 20 according to Example 6 instead of the compound 4 according to Example 1.

Example 16

An organic light emitting diode was manufactured according to the same method as Example 10 except for using the compound 44 according to Example 7 instead of the compound 4 according to Example 1.

Example 17

An organic light emitting diode was manufactured according to the same method as Example 10 except for using the compound 52 according to Example 8 instead of the compound 4 according to Example 1.

Example 18

An organic light emitting diode was manufactured according to the same method as Example 10 except for using the compound 60 according to Example 9 instead of the compound 4 according to Example 1.

Comparative Example 1

An organic light emitting diode was manufactured according to the same method as Example 10 except for using CBP instead of the compound 4 according to Example 1. The structure of the CBP is provided as follows.

Comparative Example 2

An organic light emitting diode was manufactured according to the same method as Example 10 except for using HOST1 instead of the compound 4 according to Example 1. The structure of the HOST1 is provided as follows.

Comparative Example 3

An organic light emitting diode was manufactured according to the same method as Example 10 except for using HOST2 instead of the compound 4 according to Example 1. The structure of the HOST2 is provided as follows.

The structures of NPB, BAlq, CBP, Ir(PPy)3, HOST1 and HOST2 used to manufacture an organic light emitting diode are also provided as follows.

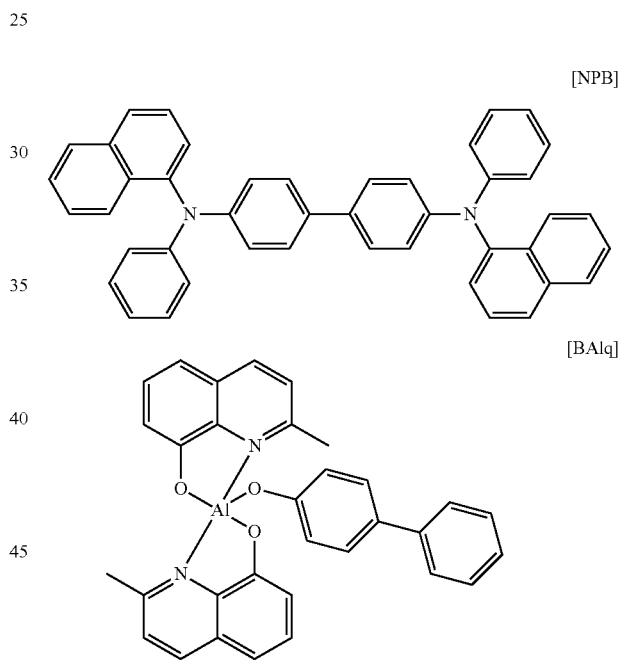

[NPB]

[BAlq]

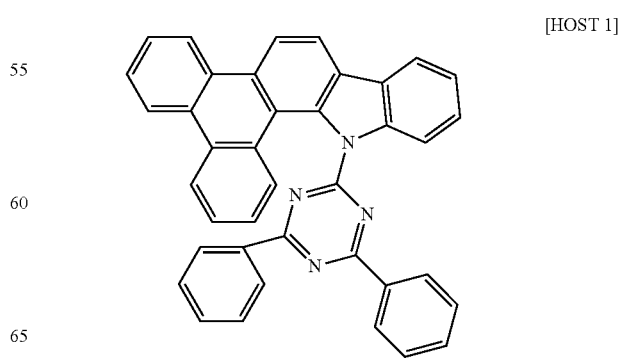

[HOST 1]

-continued

[CBP]

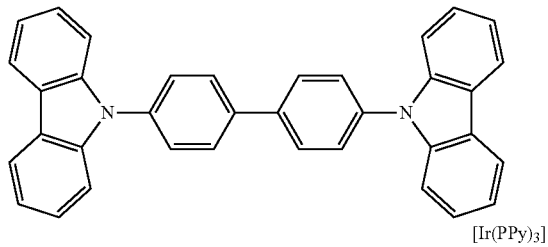

[Ir(PPy)₃]

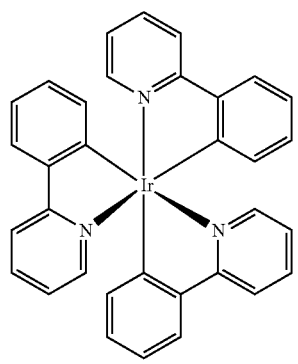

[HOST 2]

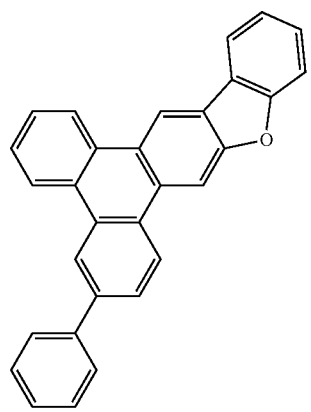

Evaluation

Current density and luminance changes depending on a voltage and luminous efficiency of each organic light emitting diode according to Examples 10 to 18 and Comparative Examples 1 to 3 were measured. The measurements were specifically performed in the following method, and the results were provided in the following Table 1.

(1) Measurement of Current Density Change Depending on Voltage Change

Current values flowing in the organic light emitting diodes were measured for, while increasing the voltage using a current-voltage meter (Keithley 2400), and the measured current values were divided by an area to provide the results.

(2) Measurement of Luminance Change Depending on Voltage Change

Luminance of the organic light emitting diodes was measured for luminance, while increasing the voltage using a luminance meter (Minolta Cs-1000A).

(3) Measurement of Luminous Efficiency

Current efficiency (cd/A) at the same current density (10 mA/cm2) were calculated by using the luminance, current density, and voltages (V) from the items (1) and (2).

TABLE 1

| Device | Compounds in emission layer | Driving voltage (V) | Color (EL color) | Efficiency (cd/A) |
|---|---|---|---|---|
| Example 10 | compound 4 | 4.3 | Green | 80.2 |
| Example 11 | compound 6 | 3.9 | Green | 85.9 |
| Example 12 | compound 7 | 3.9 | Green | 83.0 |
| Example 13 | compound 8 | 4.2 | Green | 77.1 |
| Example 14 | compound 12 | 4.5 | Green | 82.5 |
| Example 15 | compound 20 | 4.7 | Green | 79.4 |
| Example 16 | compound 44 | 4.3 | Green | 75.5 |
| Example 17 | compound 52 | 4.2 | Green | 76.2 |
| Example 18 | compound 60 | 4.5 | Green | 77.8 |
| Comparative Example 1 | CBP | 4.8 | Green | 31.4 |
| Comparative Example 2 | HOST1 | 5.5 | Green | 60.5 |
| Comparative Example 3 | HOST2 | 7.1 | Green | 35.0 |

Referring to Table 1, the compounds used for an emission layer in Examples 10 to 18 showed remarkably increased luminous efficiency but a decreased driving voltage compared with the compounds in Comparative Examples 1 to 3. Accordingly, the results show that a high efficiency device may be manufactured with a low voltage. In particular, the organic light emitting diodes respectively including the compound 6 or 7 including a fluorene group according to Example 11 or 12 showed the most excellent efficiency and a low driving voltage While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. An organic compound represented by a combination of a moiety represented by Chemical Formula 1 and a moiety represented by Chemical Formula 2:

[Chemical Formula 1]

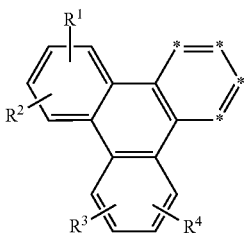

-continued

[Chemical Formula 2]

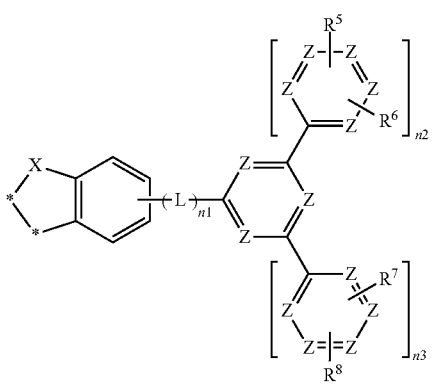

wherein, in Chemical Formula 1 and Chemical Formula 2,
X is $CR^aR^b$, $SiR^cR^d$, O, S, SO, or $SO_2$,
each Z is independently N or $CR^e$,
at least one Z is N,
$R^1$ to $R^8$ and $R^a$ to $R^e$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof,
L is a substituted or unsubstituted C1 to C20 alkylene group, a substituted or unsubstituted C6 to C30 arylene group, a substituted or unsubstituted C3 to C30 heteroarylene group, or a combination thereof,
n1 to n3 are each independently 0 or 1, and
two adjacent *s of Chemical Formula 1 are bonded with two *s of Chemical Formula 2 to form a fused ring,
wherein the organic compound is represented by Chemical Formula 4:

[Chemical Formula 4]

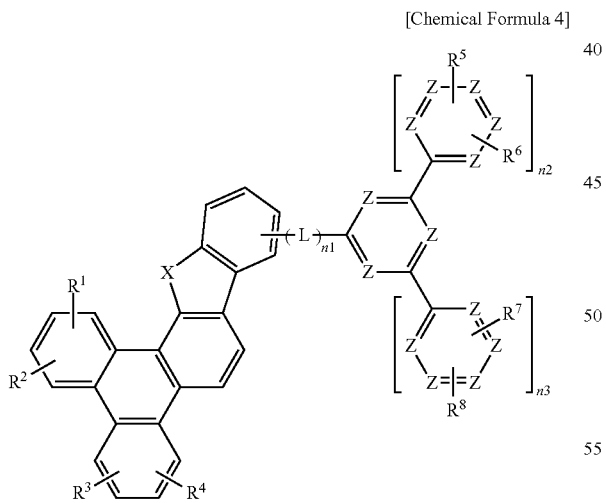

wherein, in Chemical Formula 3 and Chemical Formula 4,
X is $CR^aR^b$, $SiR^cR^d$, O, S, SO, or $SO_2$,
each Z is independently N or $CR^e$,
at least one Z is N,
$R^1$ to $R^8$ and $R^a$ to $R^e$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, L is a substituted or unsubstituted C1 to C20 alkylene group, a substituted or unsubstituted C6 to C30 arylene group, a substituted or unsubstituted C3 to C30 heteroarylene group, or a combination thereof, and
n1 to n3 are each independently 0 or 1.

2. The organic compound of claim 1, wherein the moiety represented by Chemical Formula 2 is represented by one of Chemical Formula 2-I to Chemical Formula 2-III:

[Chemical Formula 2-I]

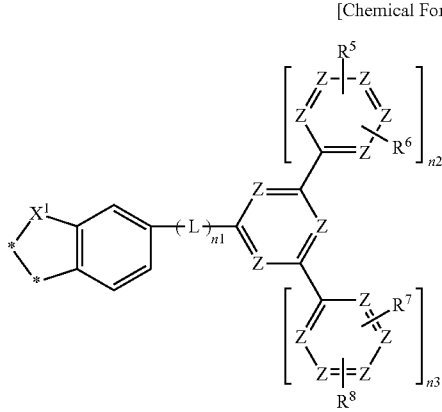

[Chemical Formula 2-II]

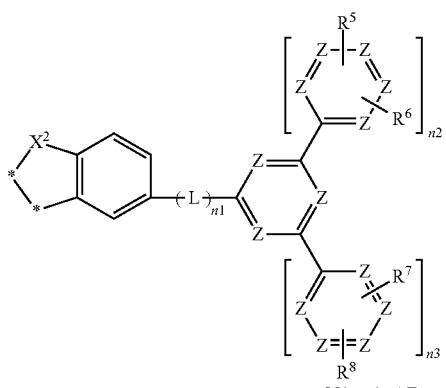

[Chemical Formula 2-III]

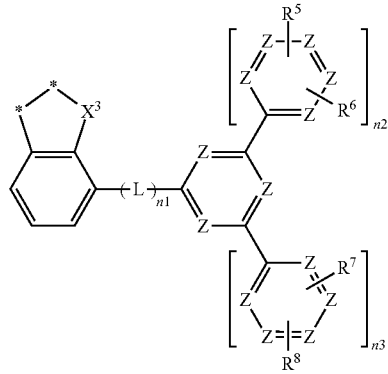

wherein, in Chemical Formula 2-I to Chemical Formula 2-III,
$X^1$ and $X^2$ are each independently $CR^aR^b$ or $SiR^cR^d$,
$X^3$ is O, S, SO, or $SO_2$,
each Z is independently N or $CR^e$,
at least one Z is N,
$R^5$ to $R^8$ and $R^a$ to $R^e$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, L is a substituted or unsubstituted C1 to C20 alkylene group, a substituted or unsubstituted C6 to C30 arylene group, a substituted or unsubstituted C3 to C30 heteroarylene group, or a combination thereof, and n1 to n3 are each independently 0 or 1, and two *s of Chemical Formulae 2-I to 2-III are bonded with two adjacent *s of Chemical Formula 1 to form a fused ring.

3. The organic compound of claim 1, wherein the moiety represented by Chemical Formula 2 is represented by a combination of Chemical Formula 2a and one of moieties listed in Group 1:

[Chemical Formula 2a]

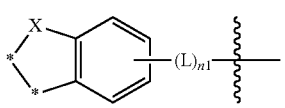

[Group 1]

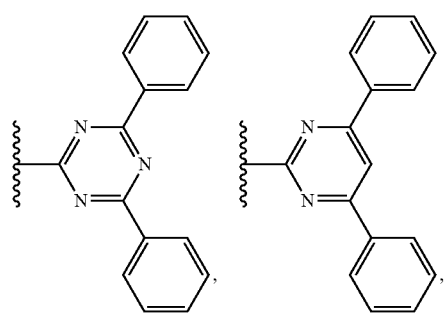

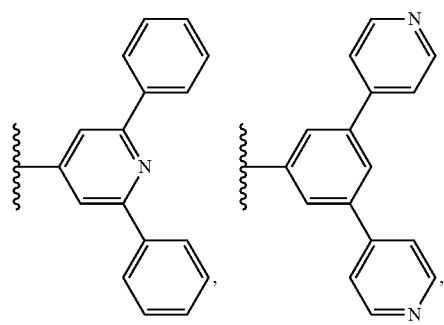

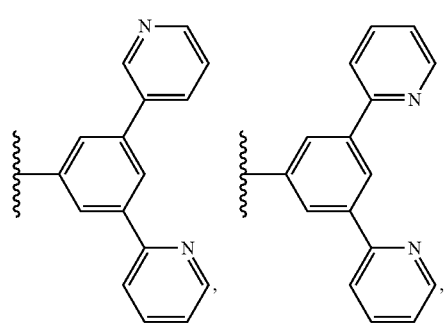

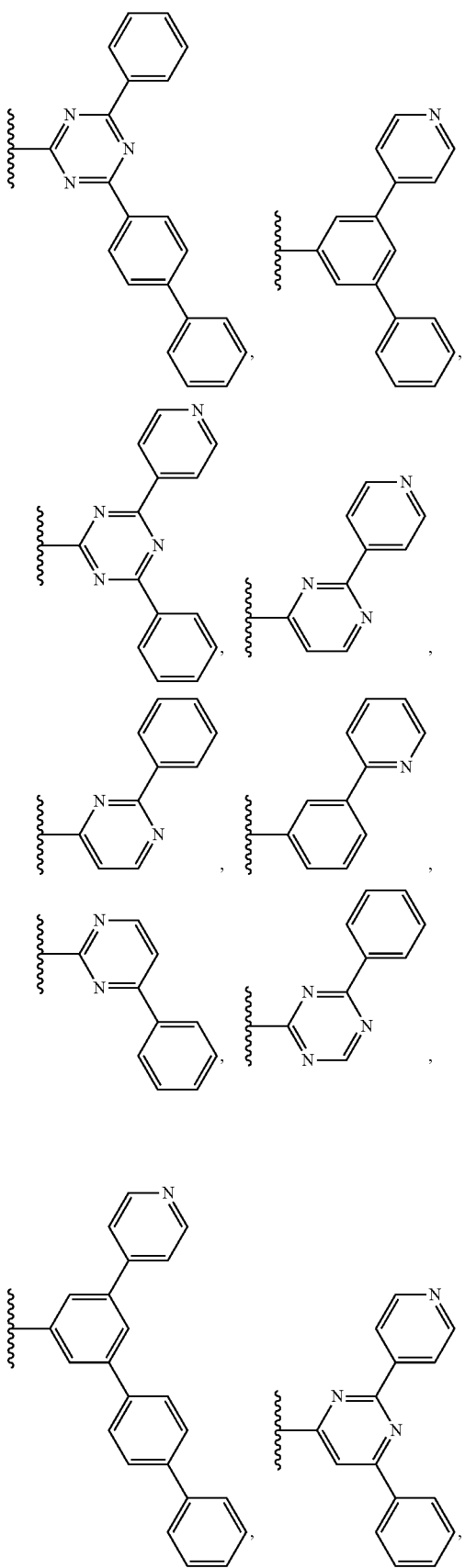

-continued

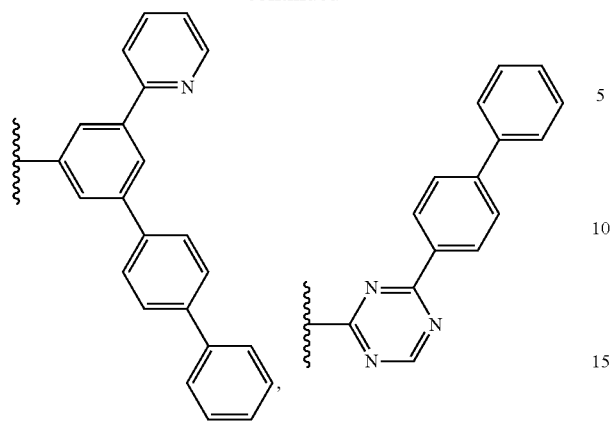

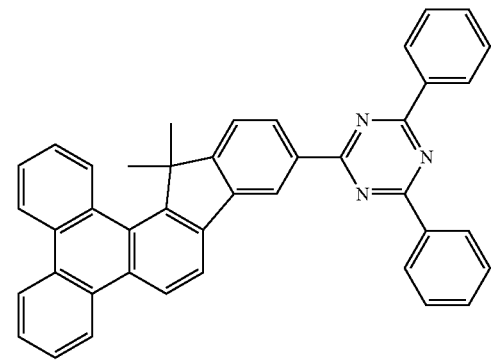

wherein, in Chemical Formula 2a and Group 1,

X is $CR^aR^b$, $SiR^cR^d$, O, S, SO, or $SO_2$, $R^a$ to $R^d$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, L is a substituted or unsubstituted C1 to C20 alkylene group, a substituted or unsubstituted C6 to C30 arylene group, a substituted or unsubstituted C3 to C30 heteroarylene group, or a combination thereof, and n1 is 0 or 1.

4. The organic compound of claim 1, wherein $R^1$ to $R^4$ are each independently hydrogen, deuterium or a substituted or unsubstituted C1 to C20 alkyl group.

5. The organic compound of claim 1, wherein the organic compound is one of the following compounds:

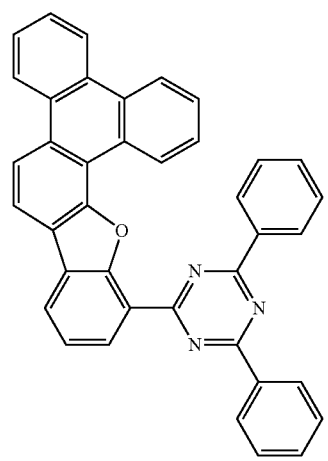

-continued

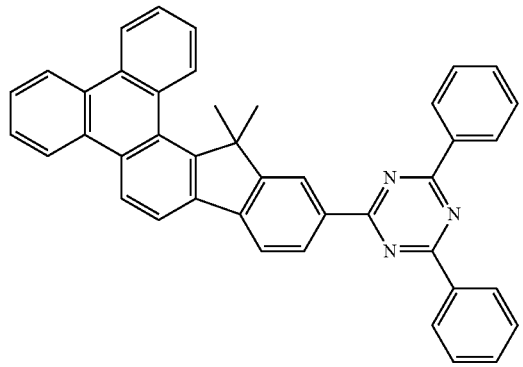

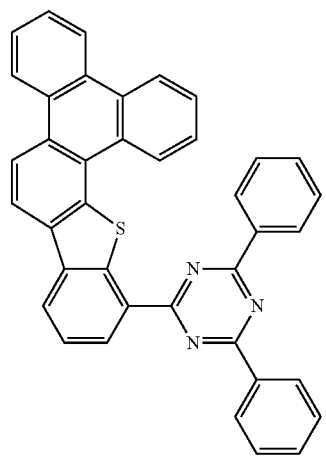

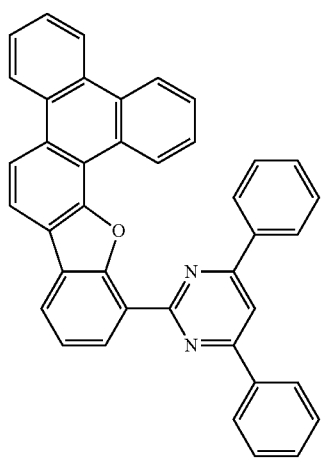

14
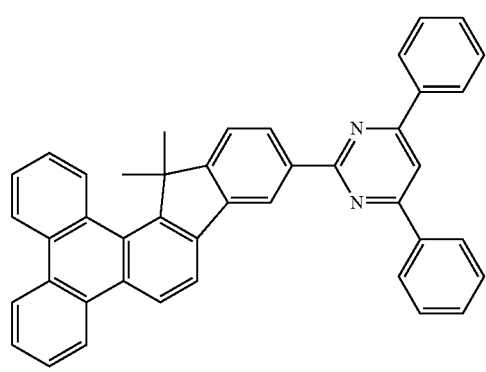
15
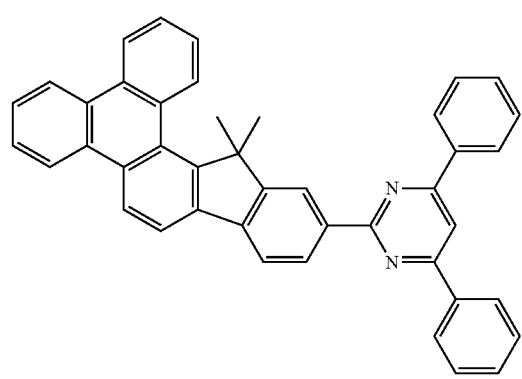
16
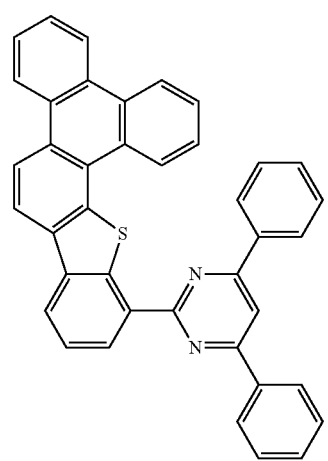
20
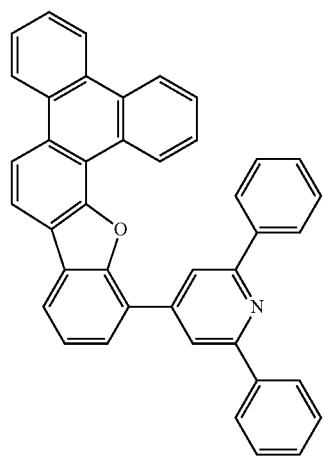
22
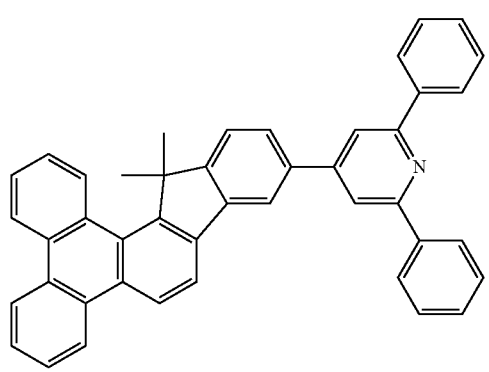
23
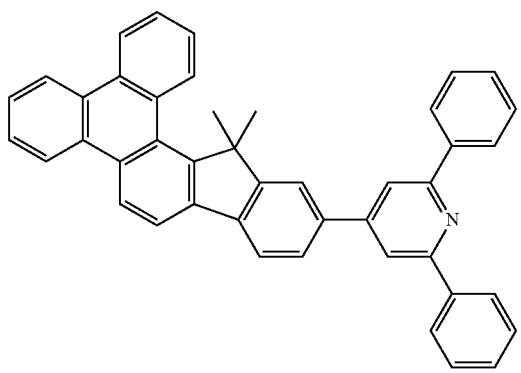

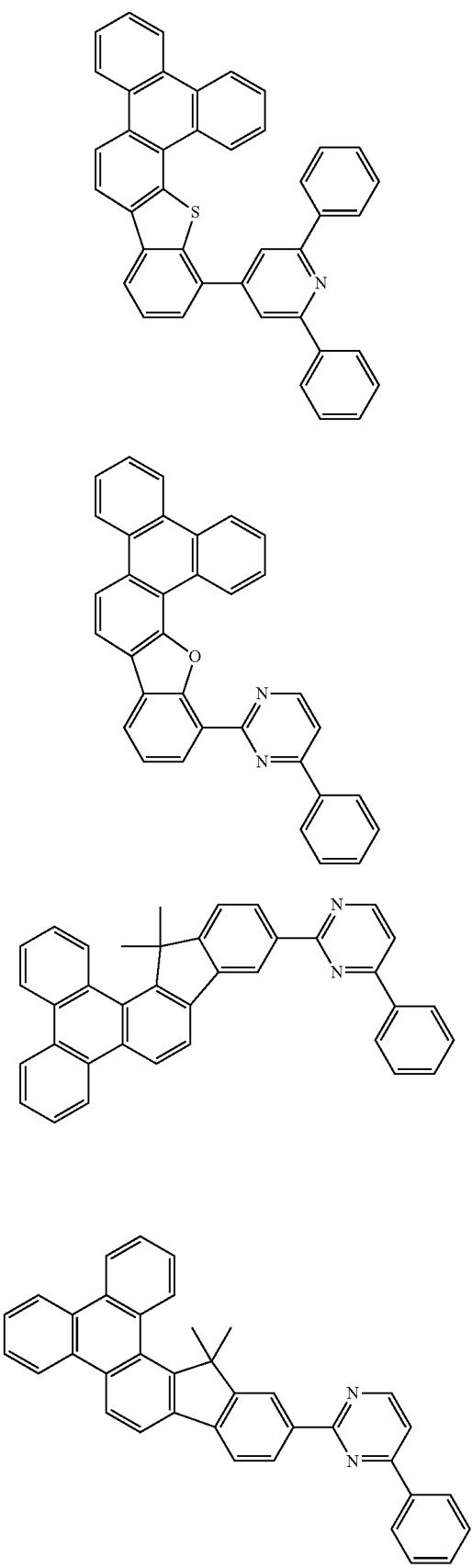
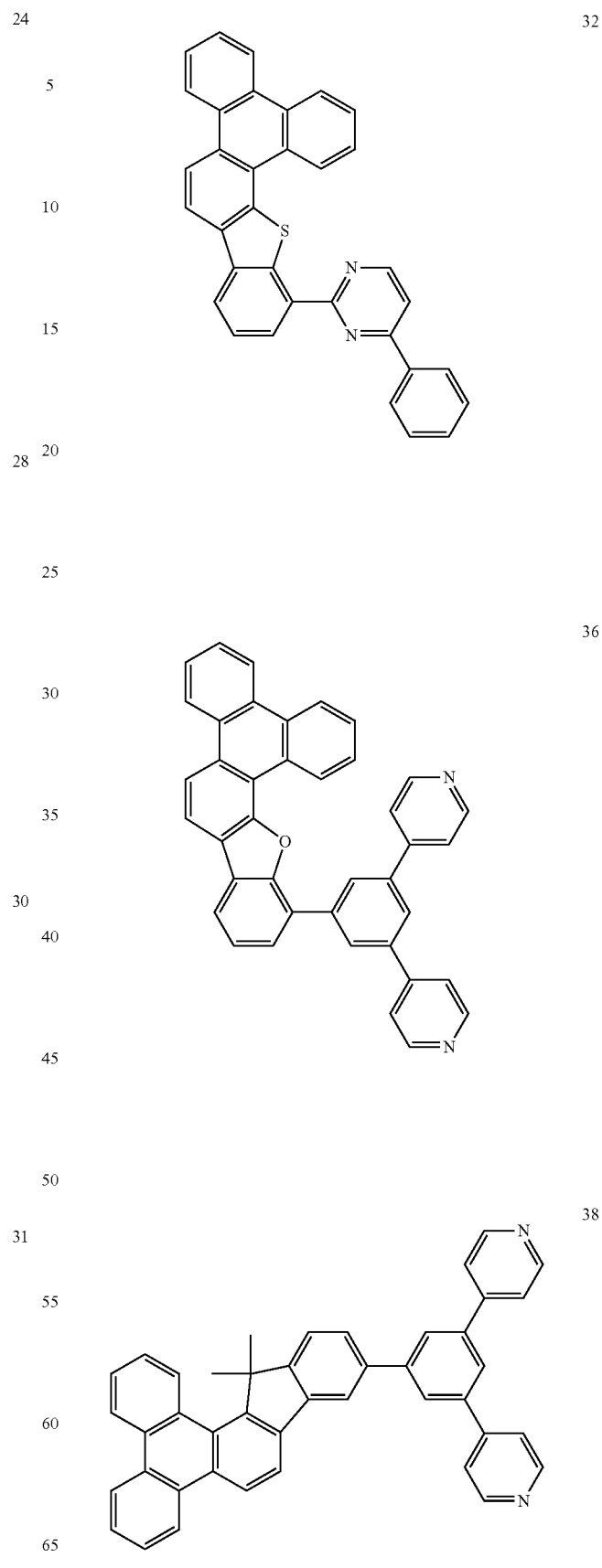

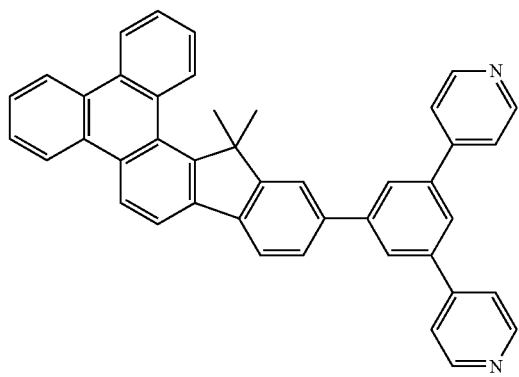
39
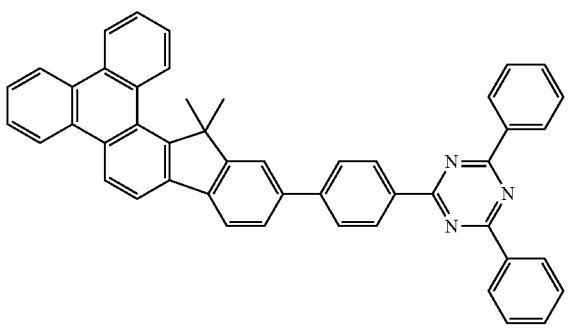
47
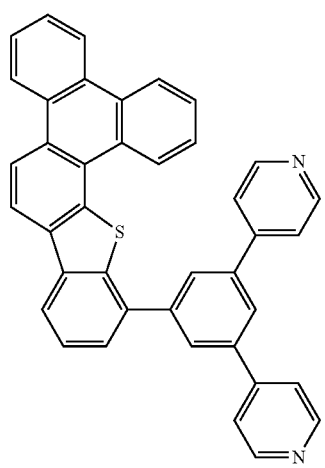
44
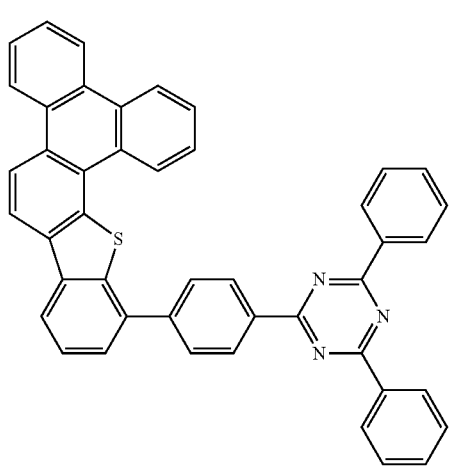
48
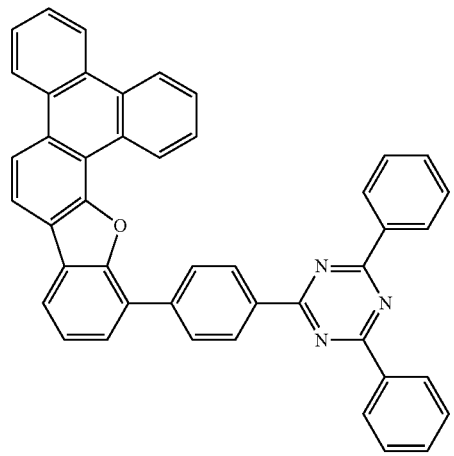
46
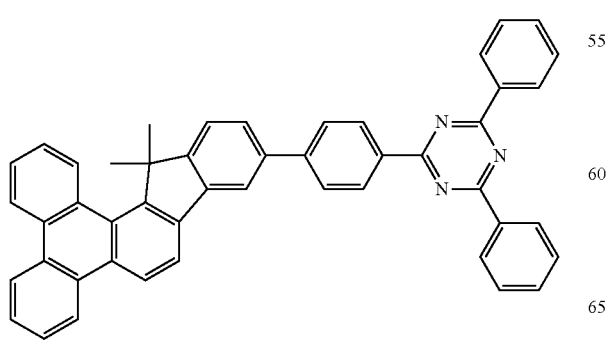
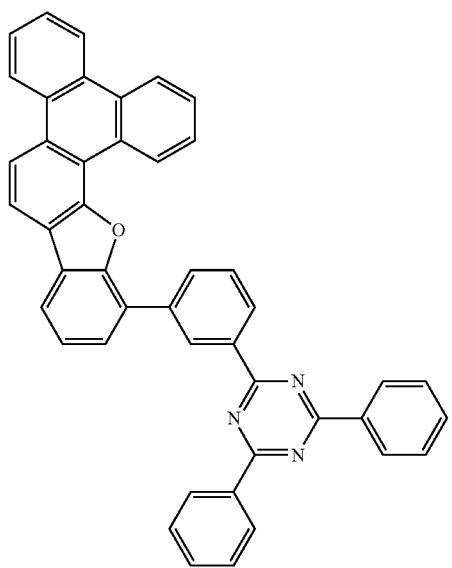
52

77
-continued
54
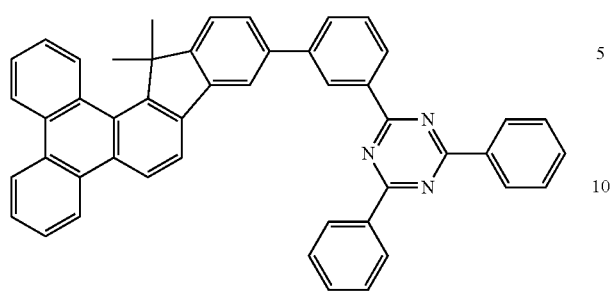
55
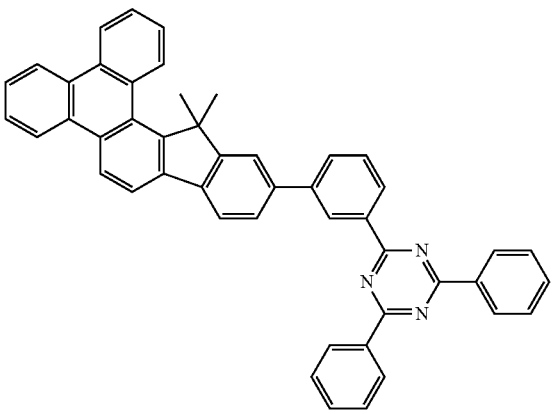
56
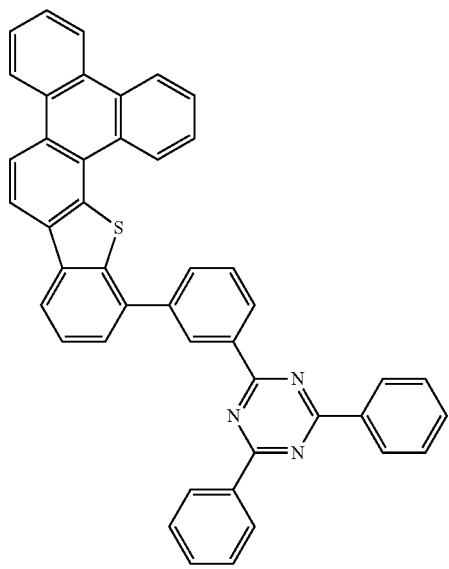
78
-continued
60
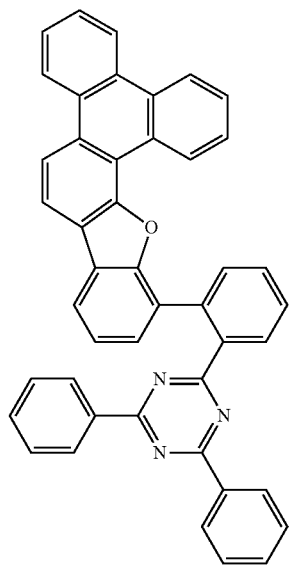
62
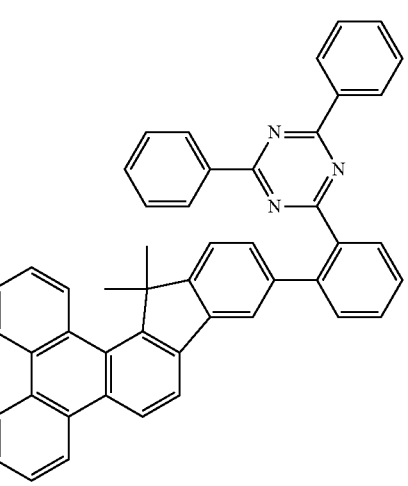
63
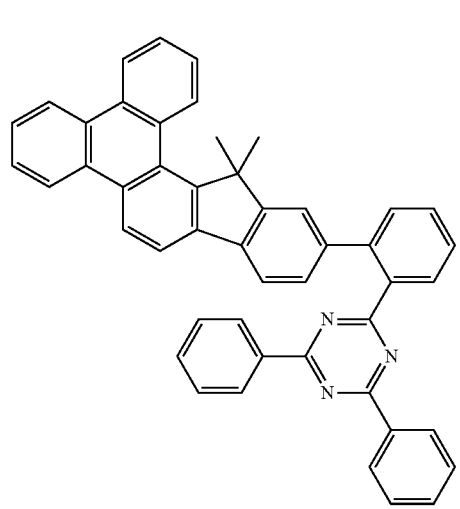

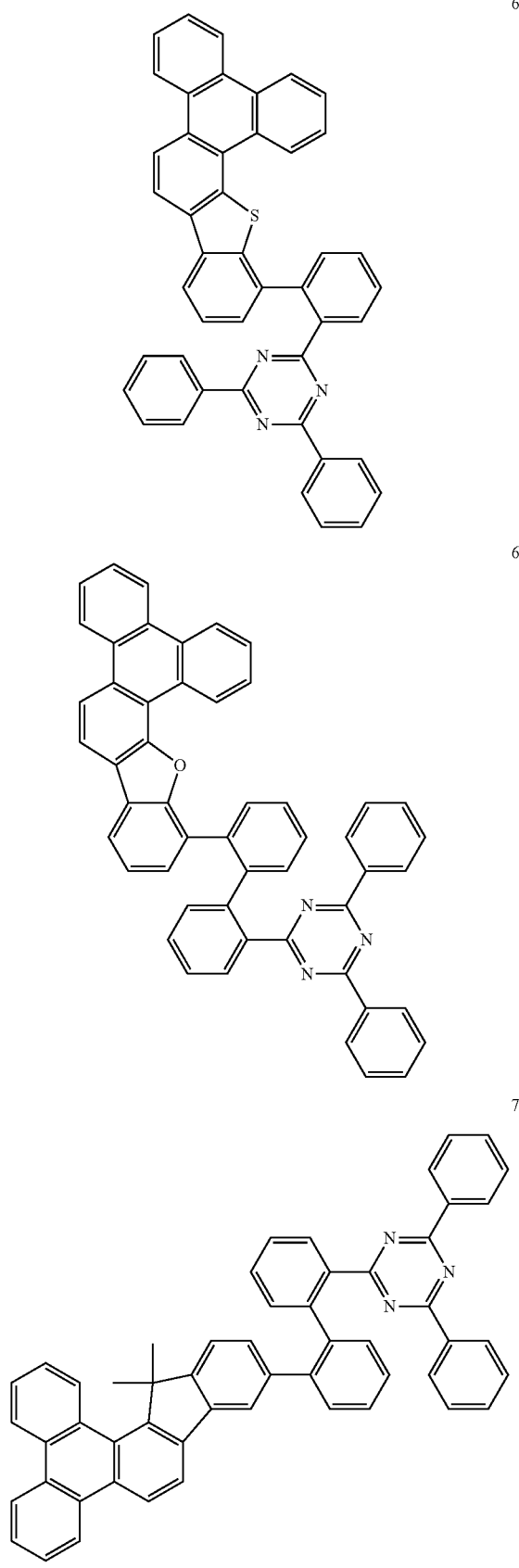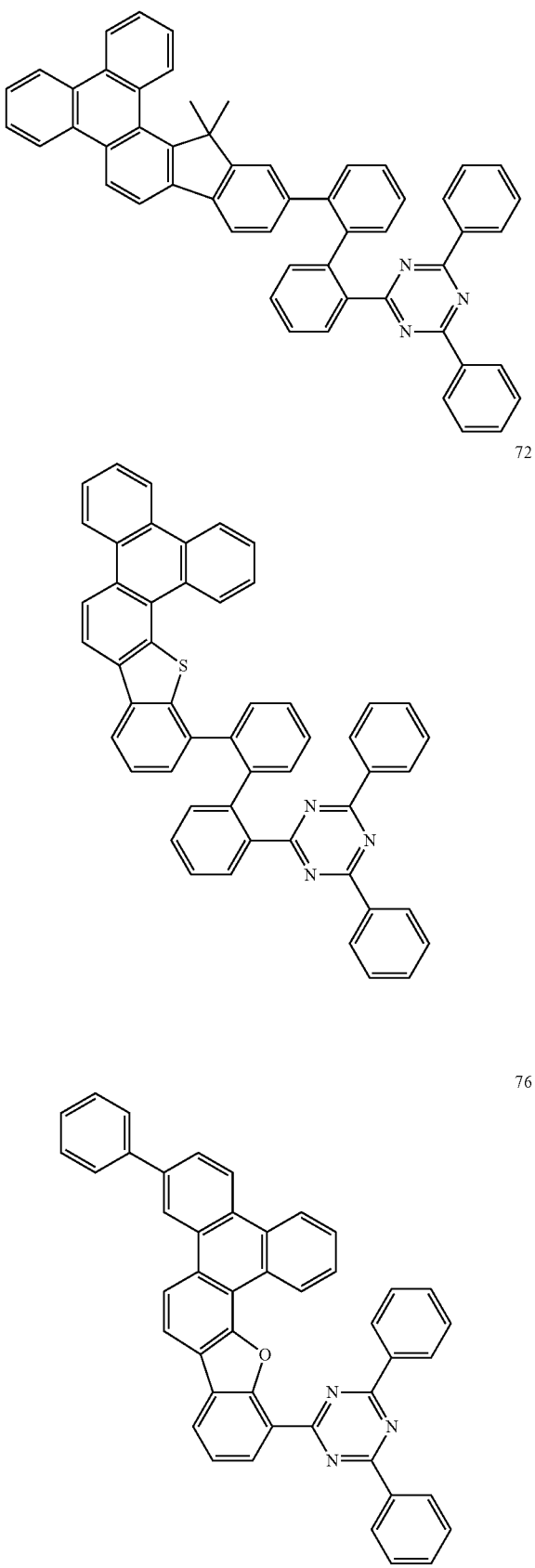

78
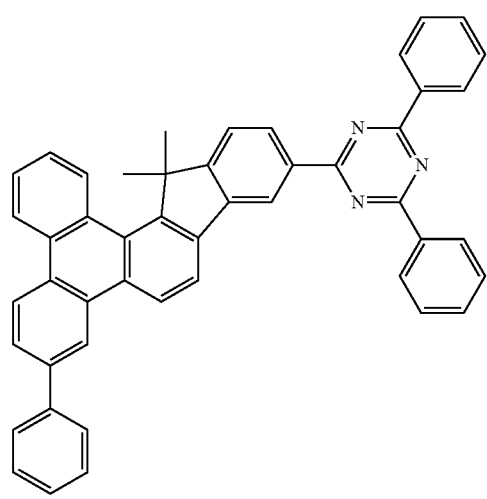
79
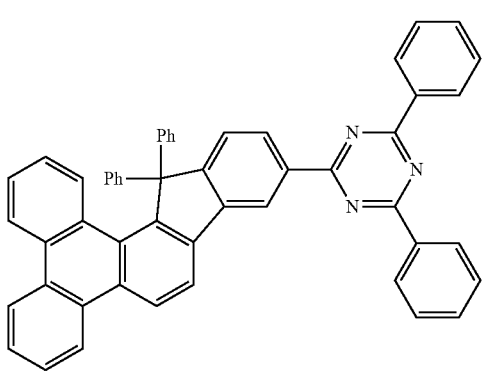
80
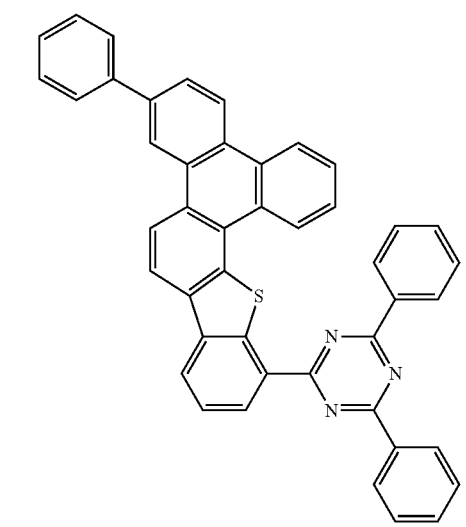
84
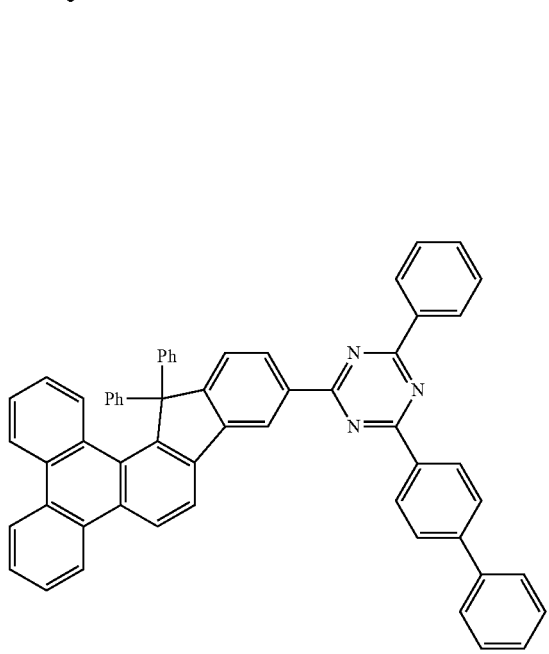
86
87
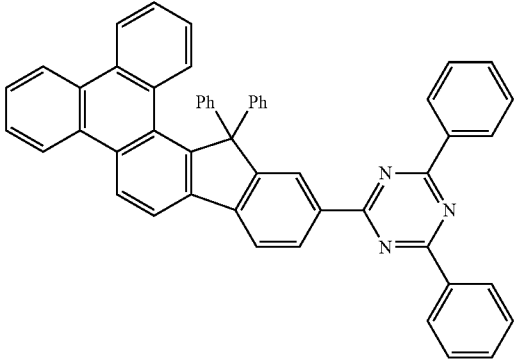

-continued

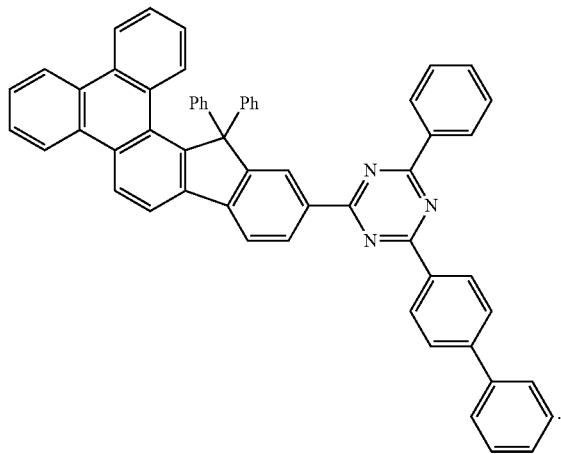

88

6. The organic compound of claim 1, wherein the organic compound has a LUMO energy of −2.0 to −2.5 eV.

7. An organic optoelectronic device, comprising:
an anode and a cathode facing each other, and
at least one organic layer between the anode and the cathode, wherein the organic layer includes the organic compound of claim 1.

8. The organic optoelectronic device of claim 7, wherein:
the organic layer includes an emission layer, and
the emission layer includes the organic compound.

9. The organic optoelectronic device of claim 7, wherein the organic compound is a host in the emission layer.

10. The organic optoelectronic device of claim 7, wherein:
the organic layer includes at least one auxiliary layer selected from a hole injection layer, a hole transport layer, an electron blocking layer, an electron transport layer, an electron injection layer, and a hole blocking layer, and
the auxiliary layer includes the organic compound.

11. A display device comprising the organic optoelectronic device of claim 7.

* * * * *